US010195319B2

(12) United States Patent
Kimura

(10) Patent No.: US 10,195,319 B2
(45) Date of Patent: Feb. 5, 2019

(54) BLOOD COMPONENT SEPARATION DEVICE

(71) Applicant: TERUMO KABUSHIKI KAISHA, Tokyo (JP)

(72) Inventor: Shigeyuki Kimura, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 389 days.

(21) Appl. No.: 14/640,080

(22) Filed: Mar. 6, 2015

(65) Prior Publication Data
US 2015/0231315 A1 Aug. 20, 2015

Related U.S. Application Data

(63) Continuation of application No. PCT/JP2012/073200, filed on Sep. 11, 2012.

(51) Int. Cl.
*A61M 37/00* (2006.01)
*A61M 1/02* (2006.01)
(Continued)

(52) U.S. Cl.
CPC ........ *A61M 1/0272* (2013.01); *A61M 1/0218* (2014.02); *A61M 1/0231* (2014.02);
(Continued)

(58) Field of Classification Search
CPC .............. A61M 1/0272; A61M 1/3693; A61M 1/3696; A61M 2202/0427; B01D 21/262; B01B 11/04; B04B 13/00
See application file for complete search history.

(56) References Cited

U.S. PATENT DOCUMENTS 4,898,675 A * 2/1990 Lavender ............ A61M 1/3496
210/321.65
5,605,842 A * 2/1997 Langley .................. A61M 1/02
435/2
(Continued)

FOREIGN PATENT DOCUMENTS

JP 2000084066 A 3/2000
JP 2003088581 A 3/2003
(Continued)

OTHER PUBLICATIONS

Kawazu et al. (JP 2005296675), English translation, originally published Oct. 2005.*
(Continued)

*Primary Examiner* — Ariana Zimbouski
(74) *Attorney, Agent, or Firm* — John R. Merkling

(57) ABSTRACT

An object of the invention is to provide a blood component separation device that can keep the concentration of anticoagulant in a predetermined blood component to a constant level to minimize aggregation of a predetermined blood component (for example, aggregation of platelets). One aspect of the present invention is a blood component separation device that separates the predetermined blood component from the blood drawn from a blood donor while supplying to the blood an anticoagulant for preventing coagulation of the blood, where an anticoagulant ratio, or a ratio of an amount of the anticoagulant supplied in relation to the blood, is set according to a hematocrit value of the blood donor so that a concentration of the anticoagulant in the predetermined blood component becomes a predetermined value.

8 Claims, 28 Drawing Sheets

(51) Int. Cl.
   *A61M 1/36*   (2006.01)
   *B01D 21/26*  (2006.01)
   *B04B 11/04*  (2006.01)
   *B04B 13/00*  (2006.01)

(52) U.S. Cl.
   CPC ........ *A61M 1/3672* (2013.01); *A61M 1/3693* (2013.01); *A61M 1/3696* (2014.02); *B01D 21/262* (2013.01); *B04B 11/04* (2013.01); *B04B 13/00* (2013.01); *A61M 2205/33* (2013.01); *A61M 2206/16* (2013.01); *A61M 2230/207* (2013.01); *B04B 2013/006* (2013.01)

(56) References Cited

U.S. PATENT DOCUMENTS

| | | | |
|---|---|---|---|
| 5,690,835 | A | 11/1997 | Brown |
| 6,743,192 | B1 | 6/2004 | Sakota et al. |
| 2002/0062100 | A1* | 5/2002 | Pierce ............... A61M 1/02 604/6.01 |
| 2003/0066807 | A1 | 4/2003 | Suzuki |
| 2003/0125881 | A1* | 7/2003 | Ryan ............... A61M 1/3496 702/19 |
| 2010/0234788 | A1* | 9/2010 | Pages ............... A61M 1/0209 604/6.04 |

FOREIGN PATENT DOCUMENTS

| | | | |
|---|---|---|---|
| JP | 2003516175 | A | 5/2003 |
| JP | 03850429 | A | 10/2005 |
| JP | 2005296675 | * | 10/2005 |
| JP | 2009226210 | A | 10/2009 |
| JP | 2012081213 | A | 4/2012 |
| WO | WO2001028621 | A | 5/2003 |
| WO | WO2008056733 | A1 | 5/2008 |
| WO | WO2012091720 | A1 | 7/2012 |

OTHER PUBLICATIONS

Extended European Search Report, European Application No. 12884688.8, dated Apr. 5, 2016.
English Translation of the International Written Opinion and Preliminary Report on Patentability for PCT Application No. PCT/JP2012/073200, dated Mar. 26, 2015, performed by the International Bureau of WIPO, 12 pages, Geneva Switzerland.
Japanese and English translation of International Search Report for PCT Application No. PCT/2012/073200, Japanese Patent Office, dated Nov. 27, 2012, p. 1-4.

* cited by examiner

FIG. 21

| HCT VALUE OF DONOR (%) | ACD CONCENTRATION IN PLATELET LIQUID (%) | AGGREGATION OF PLATELETS | |
|---|---|---|---|
| | | OCCURRENCE RATE (%) | NUMBER OCCURRED |
| ~36.9 | 17.6 | 0.284 | 57/20072 |
| 37 | 17.8 | 0.276 | 62/22454 |
| 38 | 18.0 | 0.310 | 87/28024 |
| 39 | 18.2 | 0.194 | 63/31412 |
| 40 | 18.4 | 0.188 | 65/34511 |
| 41 | 18.6 | 0.123 | 46/37299 |
| 42 | 18.8 | 0.120 | 46/38453 |
| 43 | 19.0 | 0.116 | 42/36178 |
| 44 | 19.2 | 0.072 | 23/32082 |
| 45 | 19.5 | 0.106 | 24/22720 |
| 46 | 19.7 | 0.061 | 9/14689 |
| 47.0~ | 20.0 | 0.130 | 19/14560 |

FIG. 23

| HCT VALUE (%) | ACD RATIO |
|---|---|
| 34 | 1:7.8 |
| 35 | 1:7.9 |
| 36 | 1:8.0 |
| 37 | 1:8.1 |
| 38 | 1:8.3 |
| 39 | 1:8.4 |
| 40 | 1:8.5 |
| 41 | 1:8.7 |
| 42 | 1:8.8 |
| 43 | 1:9.0 |
| 44 | 1:9.0 |
| 45 | 1:9.0 |
| 46 | 1:9.0 |
| 47 | 1:9.0 |
| 48 | 1:9.0 |
| 49 | 1:9.0 |
| 50 | 1:9.0 |
| 51 | 1:9.0 |
| 52 | 1:9.0 |

BLOOD COMPONENT SEPARATION DEVICE

TECHNICAL FIELD

The present invention relates to a blood component separation device for collecting a predetermined blood component from blood. In particular, the present invention relates to a blood component separation device that minimizes aggregation of the collected predetermined blood component (for example, aggregation of platelets).

BACKGROUND ART

Conventionally, in the field of blood drawing, a blood component, platelets for most of cases, is collected from drawn blood and other blood components are returned into the blood donor. In such operation, a blood component separation device including a centrifugal separator is used.

In recent years, in the field of radiation therapy for cancer or the like, transfusion of platelet liquid is widely performed, and high-concentration platelet liquid is necessary for the therapy. To obtain high-concentration platelet liquid, Patent Literature 1 discloses an art using a blood component separation device to temporarily store low-concentration platelet liquid in a buffy coat bag and store only high-concentration platelet liquid in a platelet intermediate bag.

As for the blood component separation device disclosed in Patent Literature 1, blood is previously stored in at least one of two blood bags, and anticoagulant, such as ACD (acid-citrate-dextrose) liquid, is added to the previously stored blood to prevent coagulation.

CITATION LIST

Patent Literature

Patent Literature 1: JP 3850429 B1
Patent Literature 2: JP 2009-226210 A

SUMMARY OF INVENTION

Technical Problem

However, in the aforementioned blood component separation device, when the ratio of the anticoagulant to be added in the blood bag (ratio of the amount of anticoagulant added in relation to the blood) is set to a same value for any blood donor (donor), the concentration of anticoagulant in the collected platelet liquid varies among blood donors having different hematocrit values (HCT value). The concentration of anticoagulant in platelet liquid is observed to have relationship with aggregation of platelets, so that when the concentration of anticoagulant in platelet liquid is low, the rate of occurrence of platelet aggregation is high. When the rate of occurrence of platelet aggregation is high, the number of platelets in the collected platelet liquid might be lower than a targeted specification for pharmaceutical preparation (causing unit shortage).

The present invention is made to solve such problem. The object of the present invention is to provide a blood component separation device that keeps the concentration of an anticoagulant in a collected predetermined blood component to a constant level to minimize aggregation of the predetermined blood component (for example, aggregation of platelets).

Solution to Problem

To solve the problem described above, one aspect of the present invention is a blood component separation device that separates a predetermined blood component from blood drawn from a blood donor while supplying to the blood an anticoagulant for preventing coagulation of the blood. The blood component separation device is configured to set an anticoagulant ratio, or a ratio of the amount of the anticoagulant supplied in relation to the blood, according to a hematocrit value of the blood donor so that a concentration of the anticoagulant in the separated predetermined blood component becomes a predetermined value.

According to the aspect, when separating the predetermined blood component from blood, the ratio of the amount of the anticoagulant supplied in relation to the blood is set according to the hematocrit value of the blood donor so as the concentration of the anticoagulant in the predetermined blood component to be kept at constant level. In this manner, the rate of occurrence of aggregation of the separated and collected predetermined blood component (for example, aggregation of platelets) can be minimized. Thus, a pharmaceutical preparation of the predetermined blood component that conforms to the targeted specification for pharmaceutical preparation can be obtained.

Furthermore, according to the aspect, the blood component separation device performs a priming step of supplying the anticoagulant, before blood drawing, to the centrifugal separator via a tube coupled to a blood drawing needle. The amount of the anticoagulant supplied which is determined by the anticoagulant ratio preferably includes the amount of the anticoagulant supplied in the priming step.

According to the aspect, the anticoagulant can surely be applied to the portion that makes contact with blood in the priming step performed before blood drawing, thereby preventing coagulation in blood when introduced.

Furthermore, according to the aspect, the blood component separation device preferably performs (a) centrifugal separation step of introducing whole blood drawn from a blood donor into the centrifugal separator to separate whole blood into a plurality of blood components, (b) circulation flow step of introducing a first blood component, among predetermined blood components separated in the centrifugal separation, among the centrifuged blood components, into the centrifugal separator together with whole blood, (c) circulation/acceleration step, performed after a predetermined amount of the first blood component is separated in the circulation flow step, of stopping the supply of whole blood to the centrifugal separator to introduce only the first blood component into the centrifugal separator, further performing circulation for a predetermined period of time, and then increasing the circulation speed so that a second blood component is separated by the centrifugal separator and collected, and (d) blood returning step, performed after collecting a predetermined amount of the second blood component in the circulation/acceleration step, of returning blood components, which are not collected, to the blood donor. A cycle from the step (a) to the step (d) is preferably performed a plurality of times.

According to the aspect, the predetermined blood component can accurately be separated from other blood components. Moreover, since the timing of collecting the blood component with high-concentration is optimized, further larger amount of the predetermined blood component can efficiently be collected.

Furthermore, in the aspect, the circulation/acceleration step includes a first collecting step of transferring a portion of the second blood component with low-concentration to a temporary storage container and a second collecting step of collecting a portion of the second blood component with high-concentration. The second blood component with low-concentration transferred to the temporary storage container may be introduced into the centrifugal separator together with the whole blood drawn in the following cycle.

Such a process can be used for BC recycling to obtain the second blood component with high-concentration, and thereby further larger amount of predetermined blood component can be collected.

In the aspect, it is preferable that the anticoagulant is ACD liquid and the predetermined blood component is platelet liquid.

According to the aspect, the ratio of the amount of ACD liquid supplied in relation to the blood can be set according to the hematocrit value of the blood donor, so that the aggregation of separated and collected platelets can be minimized. Thus, a pharmaceutical preparation of platelet liquid that conforms to the targeted specification for pharmaceutical preparation can be obtained.

Advantageous Effects of Invention

The blood component separation device according to the embodiment of the present invention can keep the concentration of anticoagulant in a collected predetermined blood component to a constant level to minimize aggregation of the predetermined blood component (for example, aggregation of platelets).

BRIEF DESCRIPTION OF DRAWINGS

FIG. 21 illustrates hematocrit values, ACD concentrations in platelet liquid, and results of aggregation of platelets of blood donors (donors), where ACD liquid is supplied to their blood by an amount set by a same ACD ratio.

FIG. 23 shows an example of the relationship between the hematocrit value (HCT value) and the ACD ratio.

DESCRIPTION OF EMBODIMENTS

Figure 1:
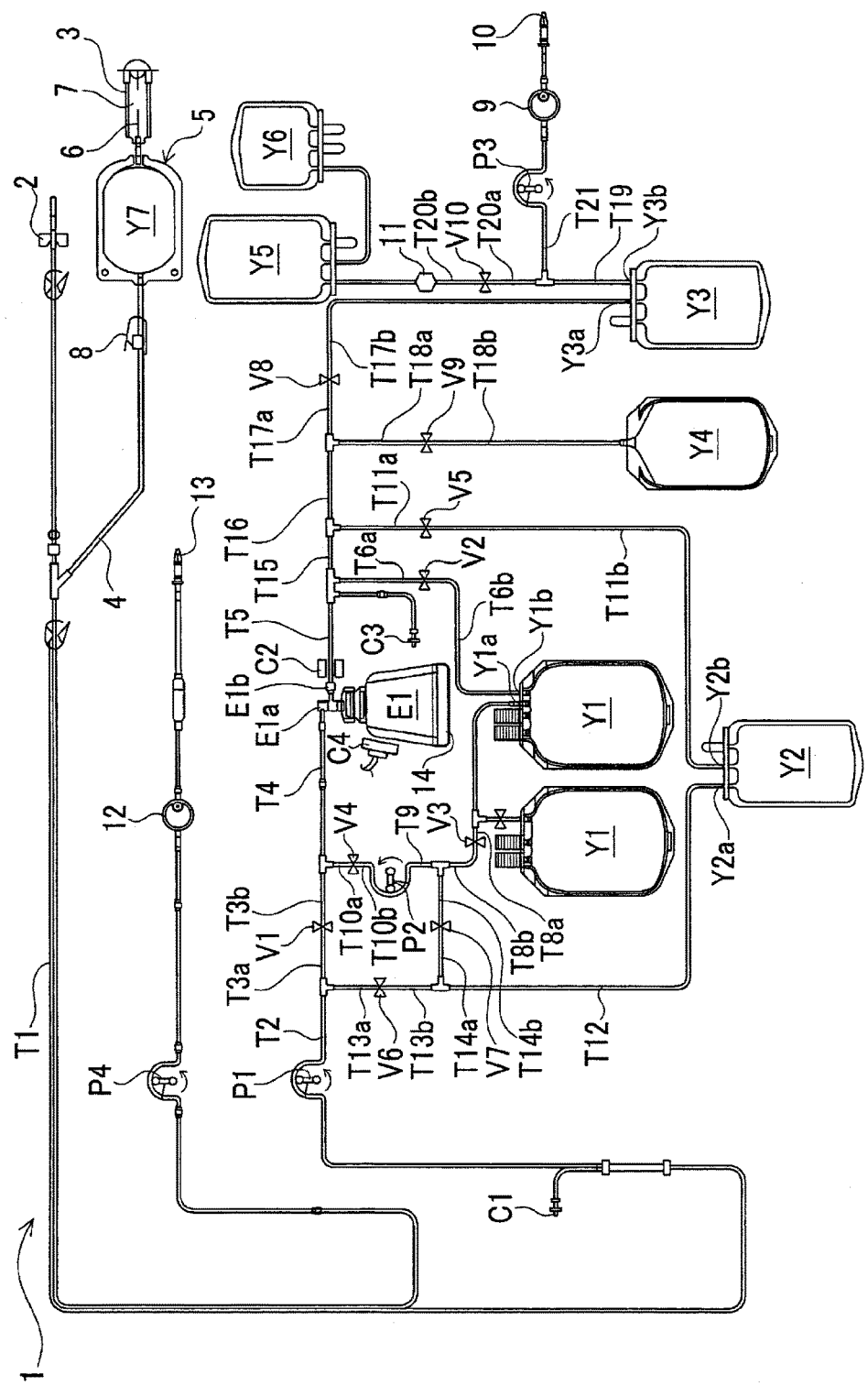
FIG. 1 illustrates a configuration of a blood component separation device according to a first working example.

Now, an embodiment of the blood component separation device according to the present invention will be described in detail referring to the drawings.

First Working Example

Figure 2:
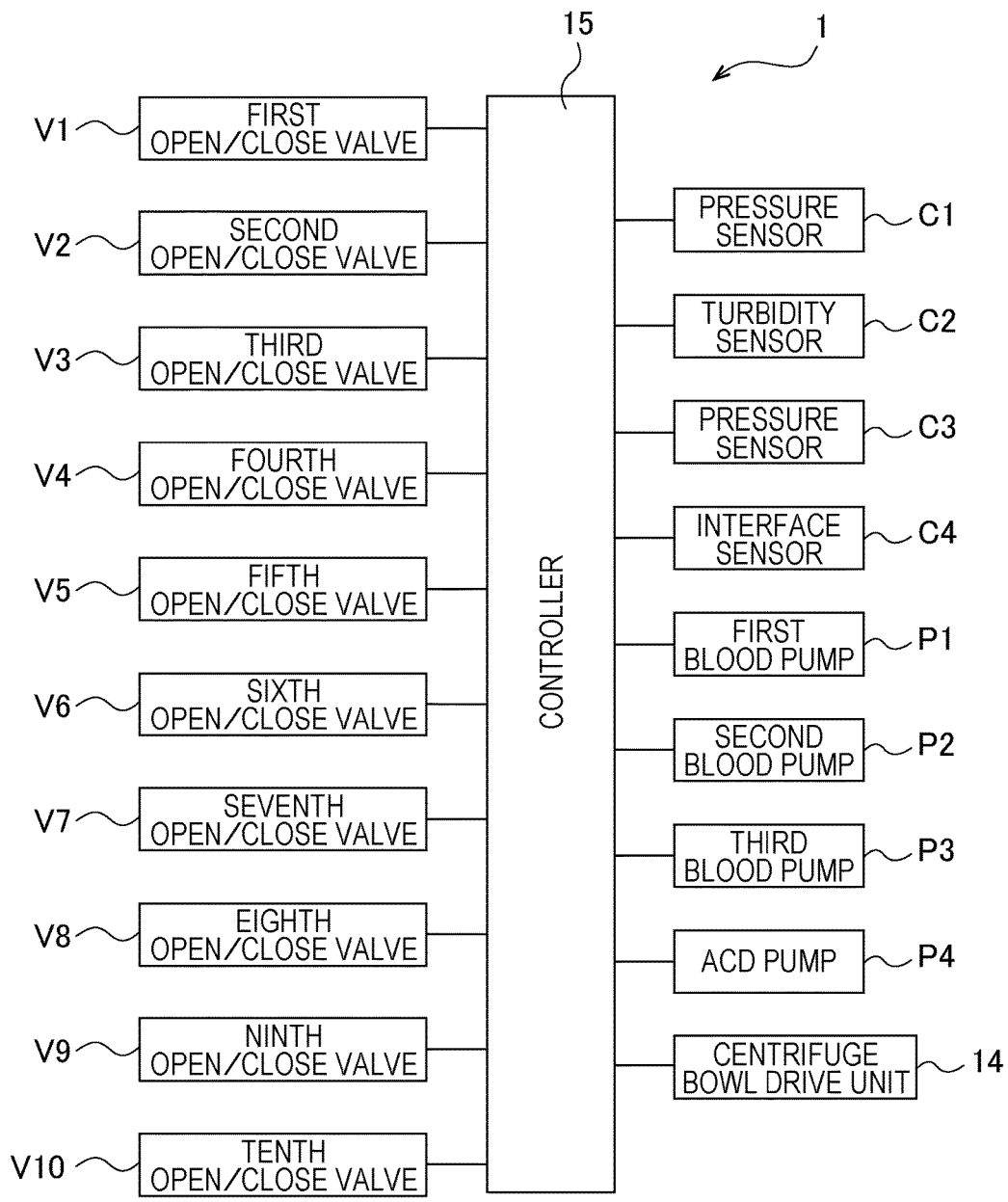
FIG. 2 is a block diagram illustrating a control system of the blood component separation device according to an embodiment.

FIG. 1 illustrates a system configuration of a blood component separation device according to a first working example. FIG. 2 is a block diagram illustrating a control system of the blood component separation device according to an embodiment.

The blood component separation device according to the embodiment includes a blood component separation circuit 1. The blood component separation circuit 1 includes an initial blood flow collecting circuit 5 composed of a blood drawing needle 2, an initial blood flow collecting bag Y7 for collecting initial blood flow, a sampling port 3, and an initial blood flow collecting line 4.

The blood component separation circuit 1 includes a centrifuge bowl E1. The centrifuge bowl E1 includes a rotor (not shown) having therein a space for storing drawn blood, a rotor drive unit 14 for rotating the rotor, an inflow port (first port E1a), and an outflow port (second port E1b), and is configured to separate blood into a plurality of blood components by rotating the rotor. The blood component separation circuit 1 includes containers for storing the blood component separated in the centrifuge bowl E1, namely, a first container (plasma bag) Y1, a second container (temporary storage bag) Y2, and a third container (platelet intermediate bag) Y3.

The blood component separation circuit 1 includes a first line, a second line, a third line, a fourth line, a fifth line, a sixth line, and a seventh line.

The first line couples the blood drawing needle 2 and the centrifuge bowl E1, and is configured with a donor tube T1, a first blood pump P1, a tube T2, a tube T3a, a first open/close valve V1, a tube T3b, and a tube T4. The second line couples the centrifuge bowl E1 and the first container Y1, and is configured with a tube T5, a tube T6a, a second open/close valve V2, and a tube T6b. The third line couples the first container Y1 and the first line, and is configured with a tube T8a, a third open/close valve V3, a tube T8b, a tube T9, a second blood pump P2, a tube T10b, a fourth open/close valve V4, and a tube T10a.

The fourth line couples the centrifuge bowl E1 and the second container Y2, and is configured with the tube T5, a tube T15, a tube T11a, a fifth open/close valve V5, and a tube T11b. The fifth line couples the second container Y2 and the first line, and is configured with a tube T12, a tube T13b, a sixth open/close valve V6, and a tube T13a. The sixth line couples the second container Y2 and the first line, similarly to the fifth line, and is configured with the tube T12, a tube T14a, a seventh open/close valve V7, a tube T14b, the tube T9, the second blood pump P2, the tube T10b, the fourth open/close valve V4, and the tube T10a. The seventh line couples the centrifuge bowl E1 and the third container Y3, and is configured with the tube T5, the tube T15, a tube T16, a tube T17a, an eighth open/close valve V8, and a tube T17b.

The blood drawing needle 2, or a drawing unit for drawing whole blood (blood) from a blood donor is coupled to the first port of the first blood pump P1 via the donor tube T1. The initial blood flow collecting bag Y7 is coupled to the blood drawing needle 2 via a branch provided on the donor tube T1 and via the initial blood flow collecting line 4. The initial blood flow collecting bag Y7 includes a sampling port 3 for transferring collected initial blood flow to a test container (not shown). The sampling port 3 is constituted with a main body, a needle 6, and a cover 7 for covering the needle 2. Furthermore, a Clamp 8 is provided on the initial blood flow collecting line to open/close the line.

The tube T2 coupled to the second port of the first blood pump P1 is branched into the tube T3a and the tube T13a. The tube T3a is coupled to the first port of the first open/close valve V1, and the second port of the first open/close valve V1 is coupled to the tube T3b. The tube T3b is branched into the tube T4 and the tube T10a. The tube T4 is coupled to the first port E1a of the centrifuge bowl E1, or a centrifugal separator for separating collected blood into a plurality of blood components. The centrifuge bowl E1 is disposed on the rotor drive unit 14 to be rotated.

The blood drawing needle 2 and the first port E1a, which is an inlet to the centrifuge bowl E1, are coupled via the first line (the donor tube T1, the first blood pump P1, the tube T2, the tube T3a, the first open/close valve V1, the tube T3b, and the tube T4).

A pressure sensor C1 is coupled to the donor tube T1.

The tube T5 coupled to the second port E1b of the centrifuge bowl E1 is branched into the tube T15 and the tube T6a. The tube T6a is coupled to the first port of the second open/close valve V2, and the second port of the second open/close valve V2 is coupled to the tube T6b. The tube T6b is coupled to the second port Y1b of the plasma bag (the first container) Y1.

The second port E1b of the centrifuge bowl E1 and the plasma bag Y1 are coupled via the second line (the tube T5, the tube T6a, the second open/close valve V2, and the tube T6b). Two plasma bags Y1 are provided, though only one plasma bag is illustrated in FIGS. 6 to 18.

The first port Y1a, or the outlet port, of the plasma bag Y1 is coupled to the tube T8a. The tube T8a is coupled to the first port of the third open/close valve V3. The second port of the third open/close valve V3 is coupled to the tube T8b, and the tube T8b is coupled to the tube T9. The tube T9 is coupled to the second port of the second blood pump P2. The first port of the second blood pump P2 is coupled to the tube T10b, and the tube T10b is coupled to the second port of the fourth open/close valve V4. The first port of the fourth open/close valve V4 is coupled to the tube T10a.

The tube T10a is coupled to the connection between the tube T3b constituting the first line and the tube T4. The plasma bag Y1 and the first line are coupled via the third line (the tube T8a, the third open/close valve V3, the tube T8b, the tube T9, the second blood pump P2, the tube T10b, the fourth open/close valve V4, and the tube T10a). The plasma bag Y1 is thus configured to selectively communicate with the inlet to, or the outlet from, the centrifuge bowl E1.

The tube T15 branched from the tube T5 branches into the tube T11a and the tube T16. The tube T11a is coupled to the first port of the fifth open/close valve V5, and the second port of the fifth open/close valve V5 is coupled to the tube T11b. The tube T11b is coupled to the second port Y2b of the temporary storage bag. That is, the second port E1b of the centrifuge bowl E1 and the temporary storage bag Y2 are coupled via the fourth line (the tube T5, the tube T15, the tube T11a, the fifth open/close valve V5, and the tube T11b).

The first port Y2a of the temporary storage bag Y2 is coupled to the tube T12, and the tube T12 is branched into the tube T13b and the tube T14a. The tube T13b is coupled to the first port of the sixth open/close valve V6, and the second port of the sixth open/close valve V6 is coupled to the tube T13a. The tube T13a is coupled to the connection between the tube T2 constituting the first line and the tube T3a.

The tube T14a branched from the tube T12 is coupled to the first port of the seventh open/close valve V7, and the second port of the seventh open/close valve V7 is coupled to the tube T14b. The tube T14b is coupled to the connection between the tube T9 and the tube T8b, and the tube T9 is coupled to the second port of the second blood pump P2.

The first port of the second blood pump P2 is coupled to the tube T10b, and the tube T10b is coupled to the first port of the fourth open/close valve V4. The second port of the fourth open/close valve V4 is coupled to the tube T10a. The tube T10a is coupled to the connection between the tube T3b constituting the first line and the tube T4. The temporary storage bag Y2 and the first line are coupled via the fifth line (the tube T12, the tube T13b, the sixth open/close valve V6, and the tube T13a) and the sixth line (the tube T12, the tube T14a, the seventh open/close valve V7, the tube T14b, the tube T9, the second blood pump P2, the tube T10b, the fourth open/close valve V4, and the tube T10a). The temporary storage bag Y2 is configured to selectively communicate with the inlet to, or the outlet from, the centrifuge bowl E1.

The tube T16 branched from the tube T15 branches into the tube T17a and the tube T18a. The tube T17a is coupled to the first port of the eighth open/close valve V8, and the second port of the eighth open/close valve V8 is coupled to the tube T17b. The tube T17b is coupled to the first port Y3a, or the inlet port, of the platelet intermediate bag (the third container) Y3. The tube T18a branched from the tube T16 is coupled to the first port of the ninth open/close valve V9, and the second port of the ninth open/close valve V9 is coupled to the tube T18b. The tube T18b is coupled to the air bag Y4. That is, the second port E1b of the centrifuge bowl E1 and the platelet intermediate bag Y3 are coupled via the seventh line (the tube T5, the tube T15, the tube T16, the tube T17a, the eighth open/close valve V8, and the tube T17b). The platelet intermediate bag Y3 is thus configured to communicate with the outlet from the centrifuge bowl E1.

A turbidity sensor C2 for detecting the concentration of platelets, and the pressure sensor C3 are attached to the tube T5 coupled to the second port E1b of the centrifuge bowl E1. The turbidity sensor C2 detects the turbidity of plasma by platelets flowing in the tube T5.

In the peripheral region of where the centrifuge bowl E1 is disposed, an interface sensor C4 for detecting the location of the interface of a buffy coat layer BC (see FIG. 3) formed in the centrifuge bowl E1 is attached.

The tube T19 coupled to the second port Y3b, or the outlet port, of the platelet intermediate bag Y3, is branched into the tube T20a and the tube T21. The tube T20a is coupled to the first port of the tenth open/close valve V10, and the second port of the tenth open/close valve V10 is coupled to the tube T20b. The tube T21 is coupled to the first port, or the outlet port, of the third blood pump P3. The second port, or the input port, of the third blood pump P3 is coupled to a Platelet additive solution bottle through a sterilizing filter 9 and a bottle needle 10. The tube T20b is coupled to the platelet bag Y5 via a white blood cell removal filter 11. The air bag Y6 is coupled to the platelet bag Y5.

An output port of the ACD pump P4 is provided on the donor tube T1. The input port of the ACD pump P4 is coupled to the output port of the sterilizing filter 12. The input port of the sterilizing filter 12 is coupled to the ACD storing bottle via a bottle needle 13.

As illustrated in FIG. 2, a controller 15 is configured with, for example, a microcomputer. The controller 15 is electrically coupled to the first blood pump P1, the second blood pump P2, the third blood pump P3, the ACD pump P4, the centrifuge bowl drive unit 14, the pressure sensor C1, the turbidity sensor C2, the pressure sensor C3, the interface sensor C4, the first open/close valve V1, the second open/close valve V2, the third open/close valve V3, the fourth open/close valve V4, the fifth open/close valve V5, the sixth open/close valve V6, the seventh open/close valve V7, the eighth open/close valve V8, the ninth open/close valve V9, and the tenth open/close valve V10.

The detection signals from the sensors C1, C2, C3, and C4 are input to the controller 15. Instructed by these detection signals, the controller 15 controls the pumps P1, P2, P3, and P4 to operate or stop, and controls the rotational direction (normal or reverse) and the rotational speed of the pumps. The controller 15 also controls the open/close valves V1, V2, V3, V4, V5, V6, V7, V8, V9, and V10 to open or close, and controls the centrifuge bowl drive unit 14 to operate as required.

As a material of the tubes, for example, thermoplastic elastomers such as polyvinyl chloride, polyethylene, polypropylene, polyester such as PET and PBT, ethylene-vinyl acetate copolymer (EVA), polyurethane, and polyester elastomer may be used. Among these materials, in particular, polyvinyl chloride is preferably used. Polyvinyl chloride not only has sufficient ductility and flexibility but also is easy to handle and suitable to be choked by a Clamp or the like.

As a material of the bags, soft polyvinyl chloride including DEHP as a plasticizer or products of polymerization or copolymerization of such olefins or diolefins as polyolefin, ethylene, propylene, butadiene, and isoprene may be used. Typical examples include ethylene-vinyl acetate copolymer (EVA), polymer blends formed between EVA and various thermoplastic elastomers, and arbitrary combinations thereof. Furthermore, PET, PBT, PCGT, or the like can be used. Among these materials, in particular, polyvinyl chloride is preferably used. Such material having high gas permeability is preferable for a container for storing platelets because the shelf life of platelets is longer. Therefore, polyolefin or DnDp-plasticized polyvinyl chloride may preferably be used for such material, or a material formed in a thin sheet may preferably be used.

Figure 3:
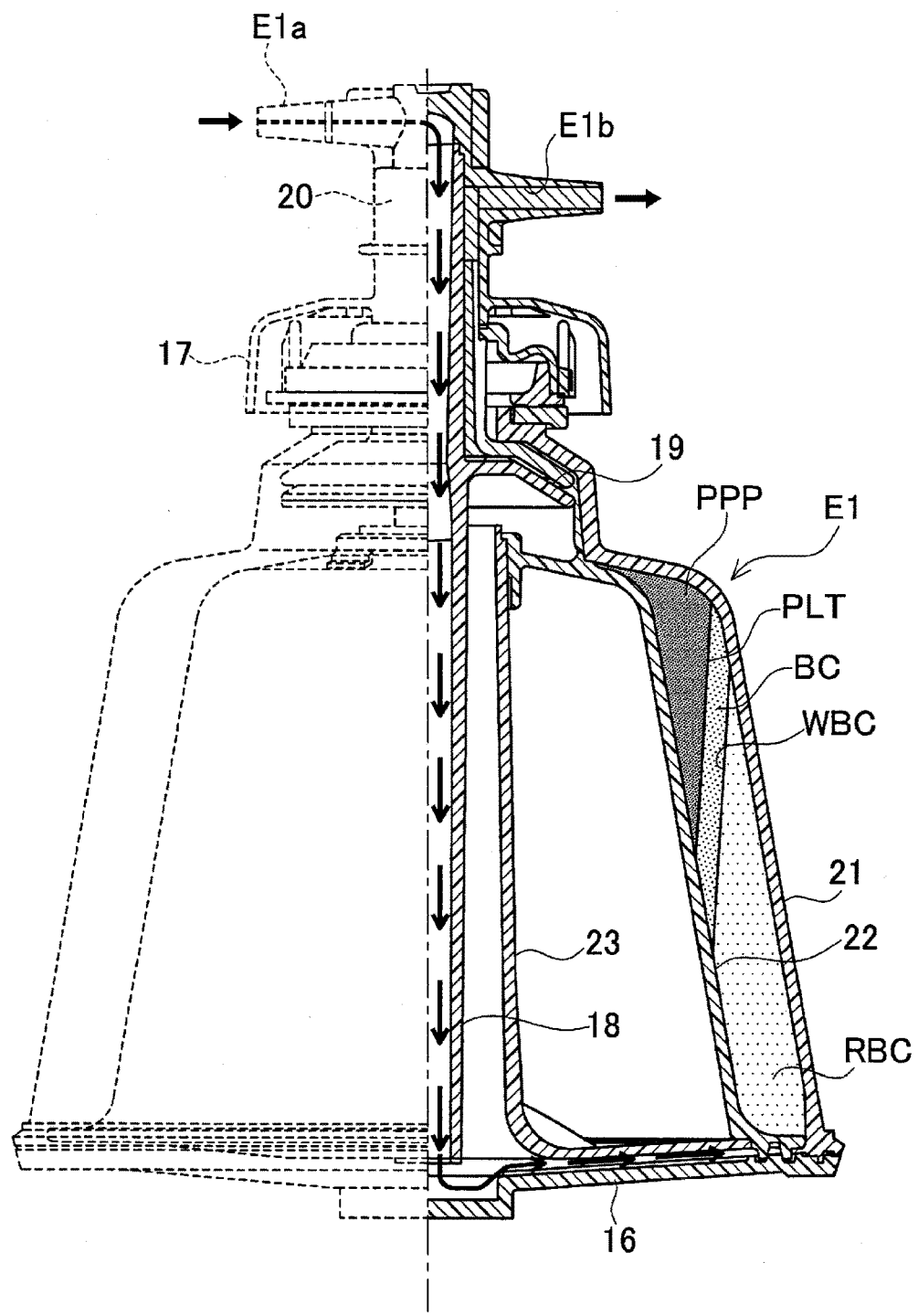
FIG. 3 illustrates a structure of a centrifuge bowl.

FIG. 3 illustrates a structure of the centrifuge bowl E1. The figure is divided by the center line, where the right hand side illustrates a sectional view and the left hand side illustrates an external view in dashed lines.

The inflow port E1a and the outflow port E1b are formed on the non-rotating fixed portion 20 in the blood component separation device. A cover 17 and an inflow tube 18 extending downward are connected to the fixed portion 20. These fixed portions integrally and rotatably support aside wall 21, an outer shell 22, an inner shell 23, and a bottom plate 16. The bottom plate 16 is coupled to the centrifuge bowl drive unit 14 by suctioning so that the rotational force can be transferred from the centrifuge bowl drive unit 14 to the bottom plate 16. FIG. 3 illustrates a state where whole blood is supplied into the centrifuge bowl E1 from the inflow port E1a and separated into blood components by centrifugal force.

That is, in the space between the outer shell 22 and the side wall 21 from the outer side to the inner side, in the descending order of specific gravity, a red blood cell layer RBC, a white blood cell layer WBC, a buffy coat layer BC, a platelet layer PLT, and a plasma layer PPP are formed by the centrifugal force. It is difficult to separate the white blood cell layer WBC and the platelet layer PLT, because their specific densities are close. Thus, the buffy coat layer BC that includes the white blood cell layer WBC and the platelet layer PLT exists. Typically, the whole blood includes about 55% of plasma PPP, about 43.2% of red blood cells RBC, about 1.35% of white blood cells WBC, and about 0.45% of platelets PLT.

The centrifuge bowl E1 has an outflow passage 19 in the inner periphery formed somewhat above the middle point of the inflow tube 18. So that the plasma layer PPP formed in the inner side of the space formed by the outer shell 22 and the side wall 21 flows out from the centrifuge bowl E1, passing through the outflow port E1b.

The operation of the blood component separation device configured as described above is illustrated in flow charts in FIGS. 4 and 5. The operation and steps performed in the blood component separation device are illustrated in FIGS. 6 to 18. The device is configured to collect platelet liquid with high-concentration. FIG. 19 is a processing drawing illustrating the operation of the blood component separation device in chronological order.

Figure 6:
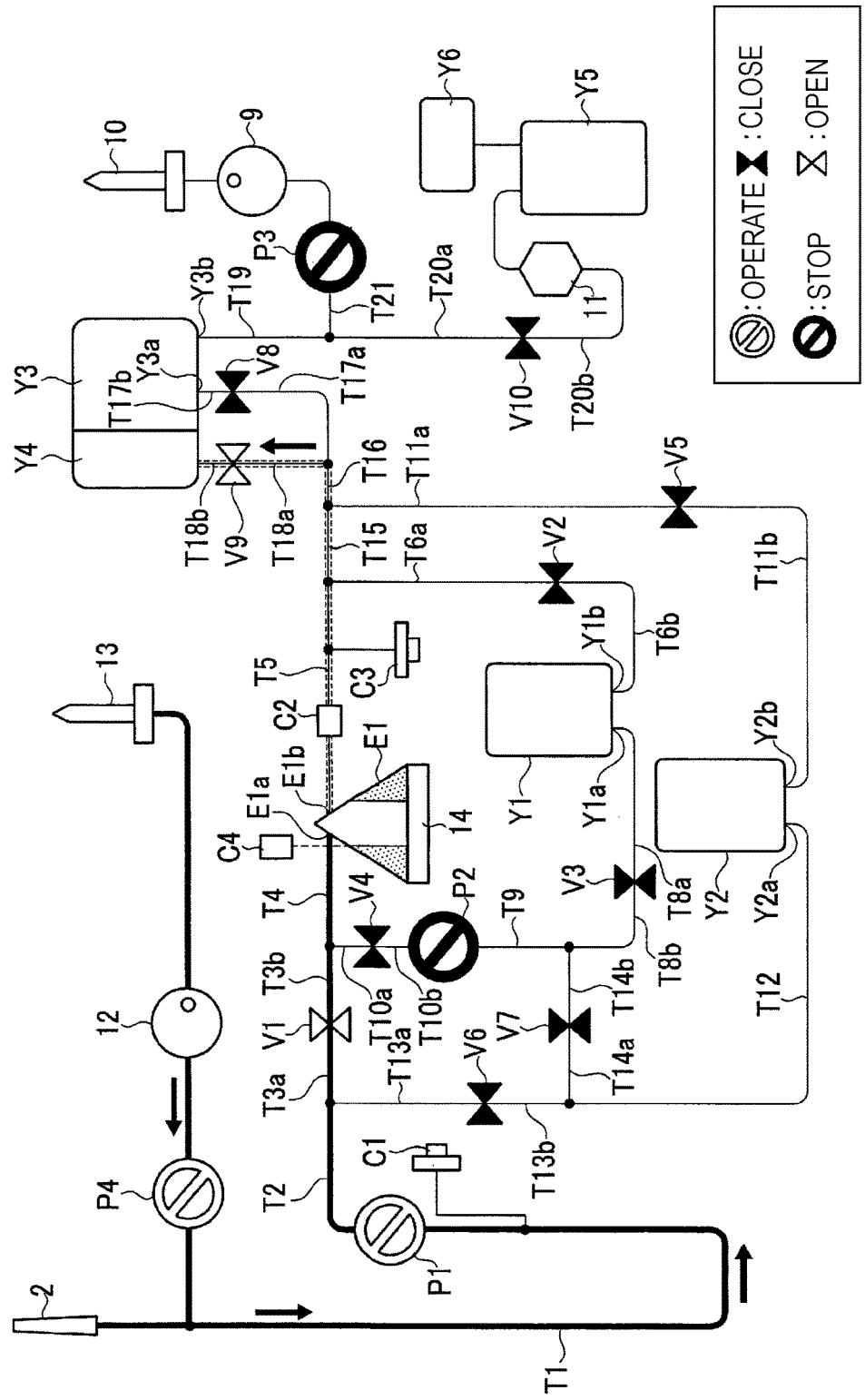
FIG. 6 illustrates a first step (starting blood drawing step) of the blood component separation device according to the first working example.

FIG. 6 illustrates a starting blood drawing step (the first step). The pump outlined with a white inside shows that the pump is operating. The pump outlined with a black inside shows that the pump is not operating. The open/close valve outlined with a white inside shows that the valve is opened. The open/close valve outlined with a black inside shows that the valve is closed.

Figure 4:
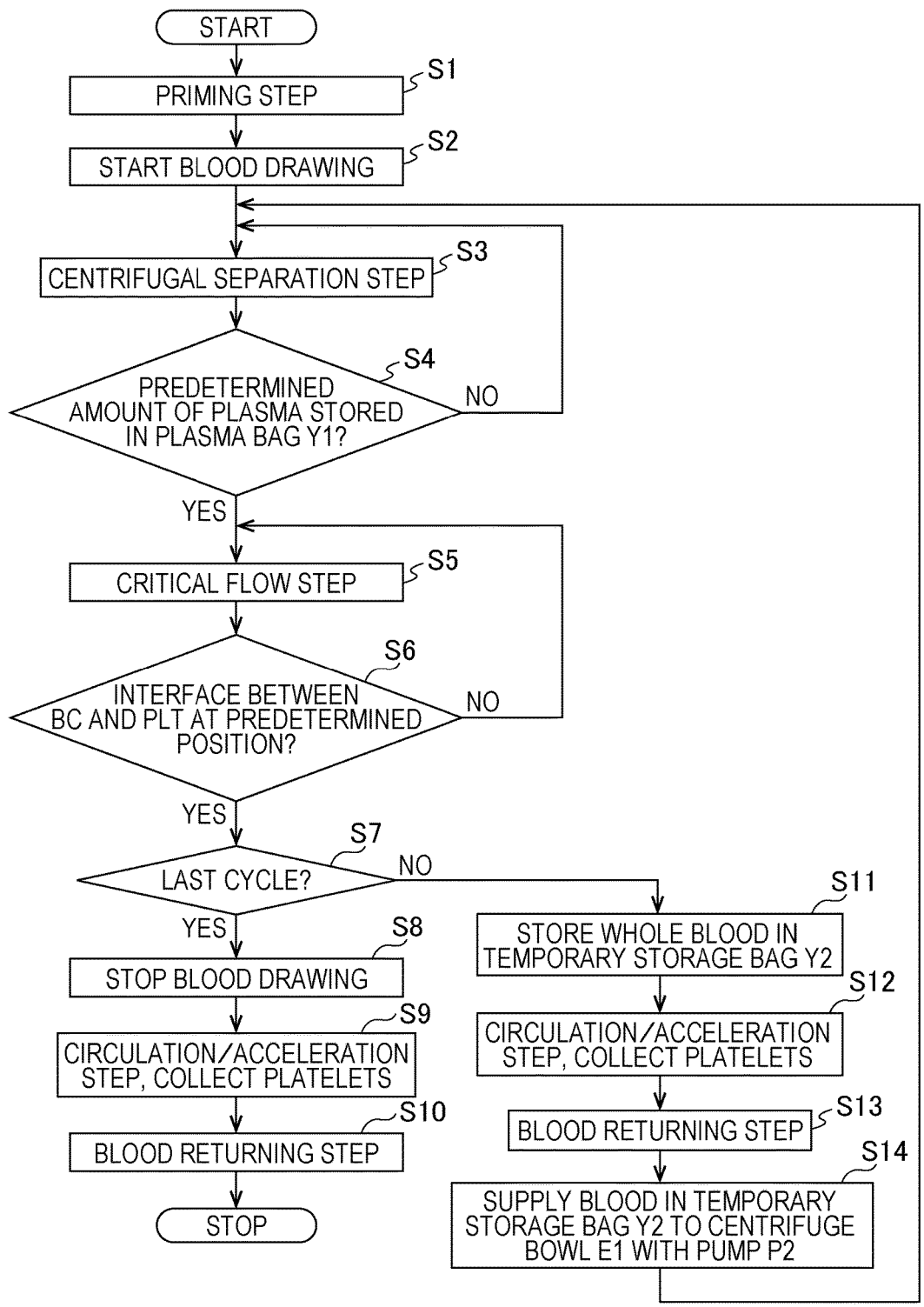
FIG. 4 is a flow chart illustrating an operation of the blood component separation device according to the first working example.

First, a priming step (S1) illustrated in FIG. 4 is performed. The ACD pump P4 and the first pump P1 are operated to supply ACD liquid, which prevents blood coagulation, to the centrifuge bowl E1 via the opened first open/close valve V1, thereby performing the priming step (S1) for the centrifuge bowl E1, the first pump P1, etc. The priming step is performed to previously apply the ACD liquid to portions in the donor tube T1, the first pump P1, the centrifuge bowl E1, etc., which are to make contact with blood, so that the blood does not coagulate when introduced. From the priming step, the centrifuge bowl drive unit 14 rotates the centrifuge bowl E1 at a predetermined rotational speed. For example, 30 ml of the ACD liquid is supplied in the priming step (S1).

When the priming step (S1) is finished, the blood drawing needle 2 pierces the blood donor, and drawing of whole blood (S2) starts. After the blood drawing needle 2 piercing the blood donor, first, the initial blood flow is collected in the initial blood flow collecting bag Y7 of the initial blood flow collecting circuit (see FIG. 1). In the initial state, the branch provided on the donor tube T1 provides communication between the blood drawing needle 2 and the initial blood flow collecting line 4 (see FIG. 1). When a predetermined amount of blood is stored in the initial blood bag Y7, the initial blood flow collecting line 4 is choked by the Clamp 8 (see FIG. 1) to secure a flow passage in the donor tube T1 toward the first blood pump P1.

The ACD pump P4 is operated to supply ACD liquid to the donor tube T1 so that the ACD liquid is mixed with the whole blood, which is then supplied to the centrifuge bowl E1. When whole blood is supplied to the rotating centrifuge bowl E1, the air inside the centrifuge bowl E1 (shown in dashed lines) is pushed by the plasma to flow out through the outflow passage 19 (see FIG. 3) located in the inner periphery of the centrifuge bowl E1, as illustrated in FIG. 6. The air then flows through the opened ninth open/close valve V9 and is stored in the air bag Y4.

In the centrifuge bowl E1, as illustrated in FIG. 3, the supplied whole blood is separated into components by the centrifugal force applied in the bowl.

Figure 7:
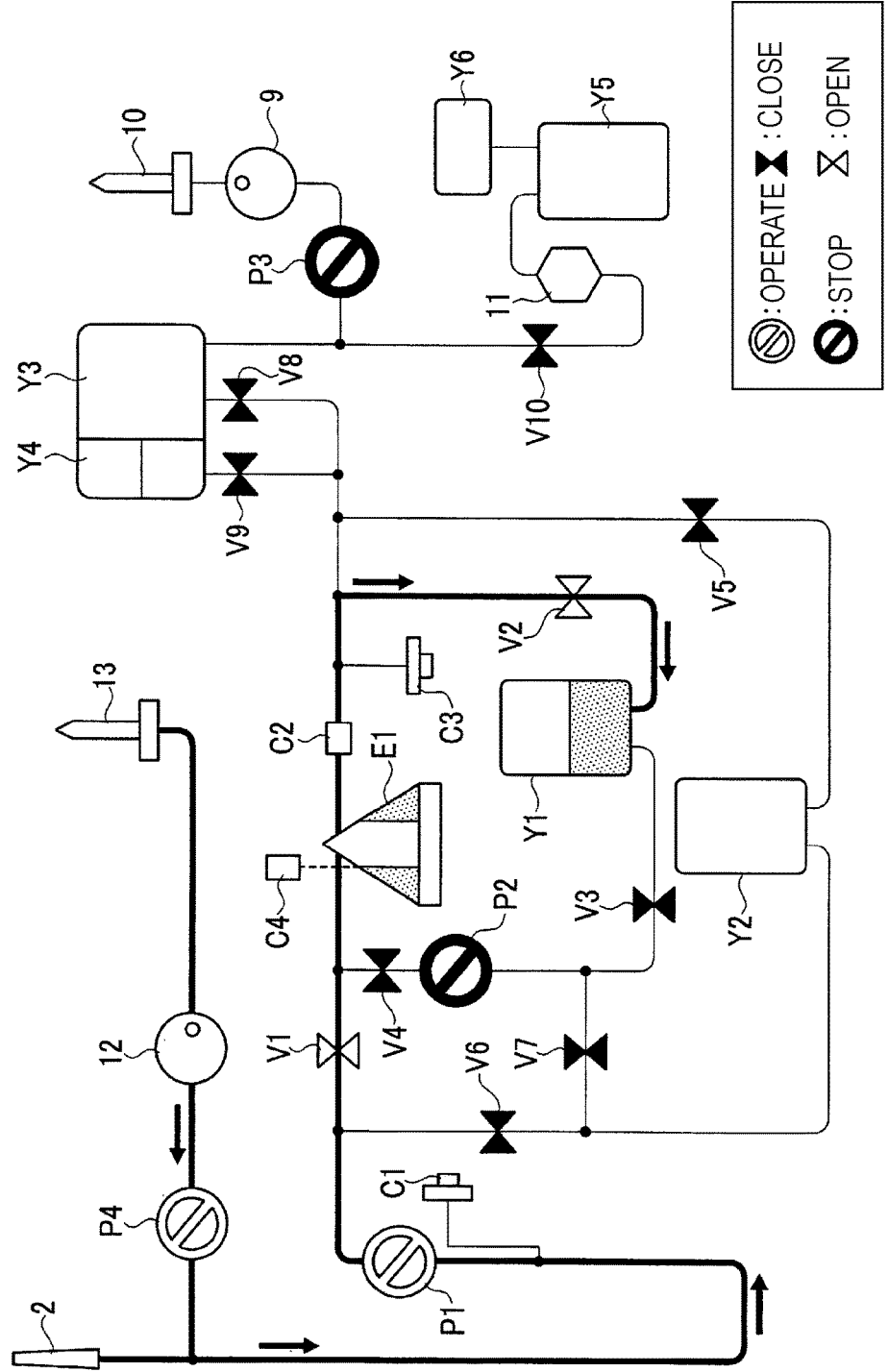
FIG. 7 illustrates a second step (centrifugal separation step).

Then when the turbidity sensor C2 detects that the fluid flowing in the tube has changed from air to plasma, the ninth open/close valve V9 is closed and the second open/close valve V2 is opened to store the plasma spilled out from the centrifuge bowl E1 in the plasma bag Y1, as illustrated in FIG. 7. Thus the centrifugal separation step (S3) is performed. As illustrated in FIG. 3, first, only plasma comes out from the centrifuge bowl E1.

Figure 8:
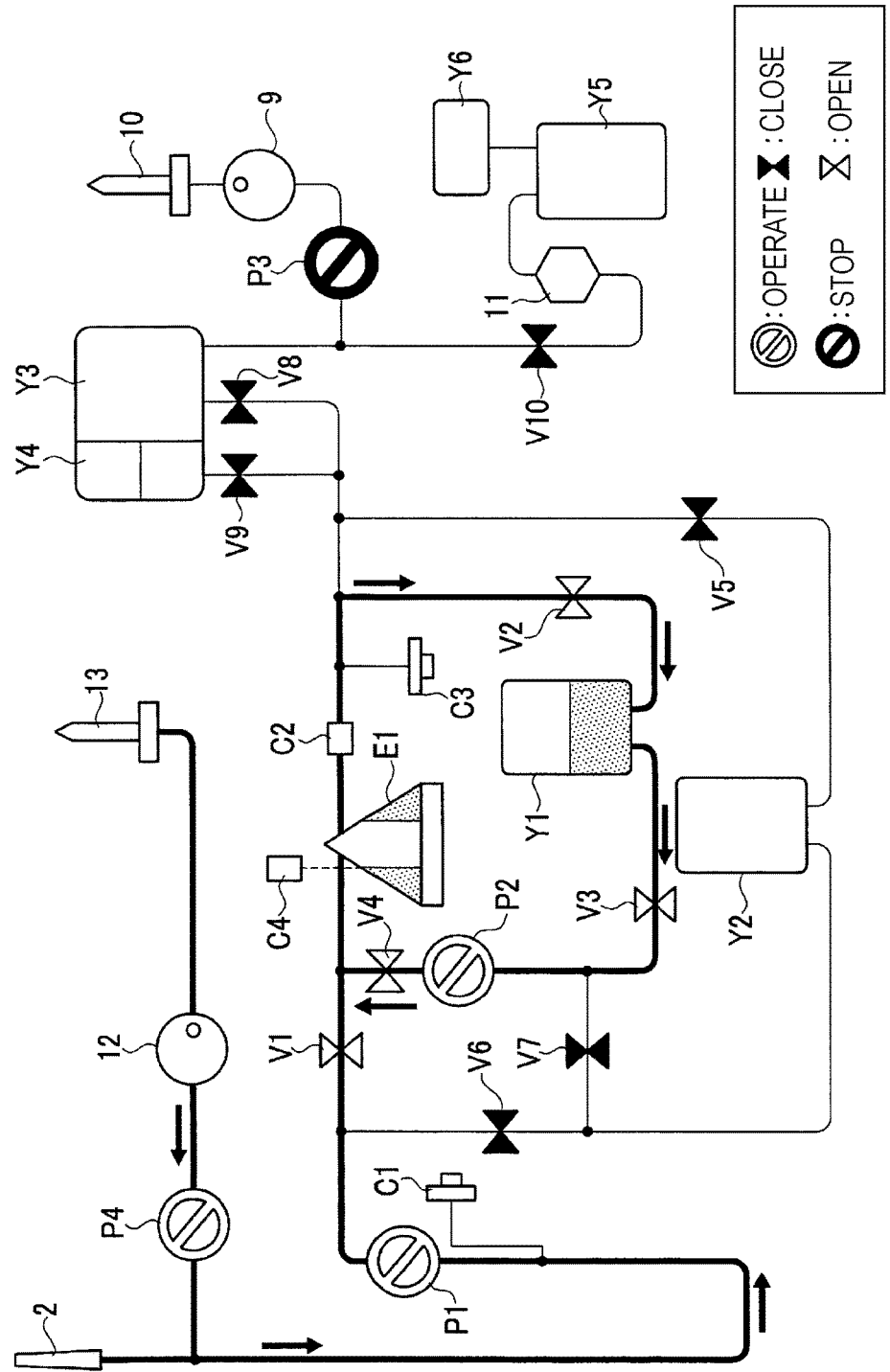
FIG. 8 illustrates a third step (critical flow step).

Then when a certain amount of plasma (30 ml for the working example) is stored in the plasma bag Y1 (S4: YES), the third open/close valve V3 is opened, the second blood pump P2 is operated, and the fourth open/close valve V4 is opened to draw whole blood from the blood donor, mix the whole blood with the plasma stored in the plasma bag Y1, and supply the mixture of the whole blood and the plasma to the centrifuge bowl E1, as illustrated in FIG. 8. Thus, a third step (critical flow step) (S5) is performed. These are performed in a critical flow period TE shown in FIG. 19.

Figure 9:
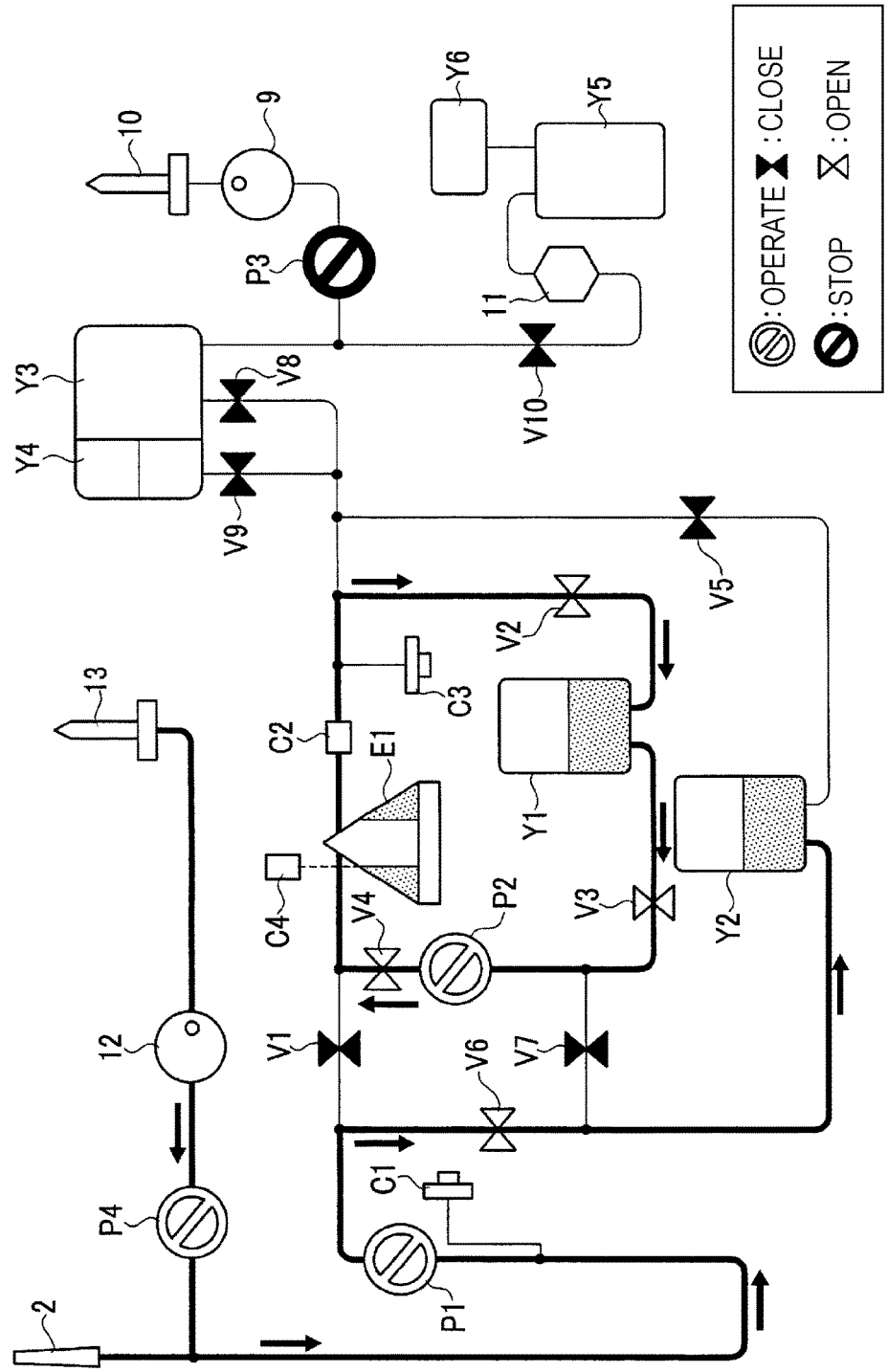
FIG. 9 illustrates a circulation step in a fourth step (circulation/acceleration step).

When the interface sensor C4 detects that the interface between the buffy coat layer BC and the red blood cell layer RBC in FIG. 3 has come to a predetermined position (S6: YES), the first open/close valve V1 is closed with the second open/close valve V2, the third open/close valve V3, and the fourth open/close valve V4 opened, and the second blood pump P2 is kept operating as illustrated in FIG. 9. The plasma in the plasma bag Y1 flows through the third open/close valve V3, the second blood pump P2, the fourth open/close valve V4, the centrifuge bowl E1, and the second open/close valve V2 to return to the plasma bag Y1. A circulation step (fourth step) in the circulation/acceleration step is thus performed. This is performed in a circulation period TF shown in FIG. 19.

At the same time, whether the present cycle is the last cycle is determined. When the present cycle is not the last cycle (S7: NO), the sixth open/close valve V6 is opened, with the first blood pump P1 kept operating, to store the drawn whole blood in the temporary storage bag Y2 (S11). In other words, the drawing of whole blood can be continued by storing the drawn whole blood in the temporary storage bag Y2. The drawing of whole blood is continued until the completion of the circulation/acceleration step or until a previously determined time elapses or a previously determined amount of whole blood is drawn. In the last cycle (S7: YES), the first blood pump P1 is stopped to halt the blood drawing (S8).

In the circulation step in the circulation/acceleration step of the working example, the circulation speed is set higher than the critical flow step, where the plasma circulates at the speed of 100 ml/min, flowing through the centrifuge bowl E1 within 30 to 40 seconds. In this manner, the concentration of particulates in the buffy coat layer BC in FIG. 3 is reduced, whereby the white blood cell layer WBC having a larger specific gravity than platelets sediments in the outer side of the buffy coat layer BC. That is, the platelet layer PLT and the white blood cell layer WBC can further distinctly be separated.

Figure 10:
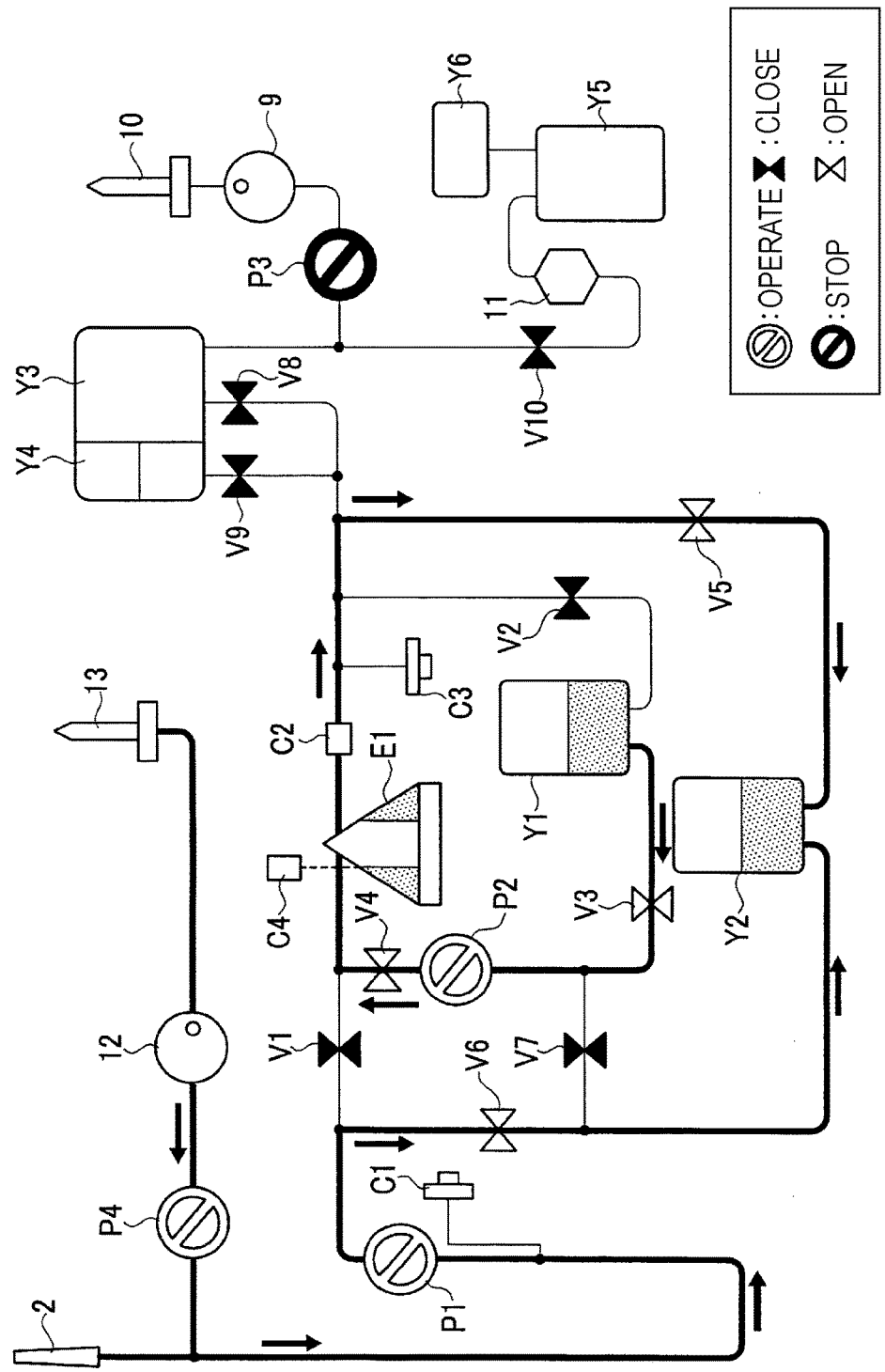
FIG. 10 illustrates a step of collecting platelet liquid with low-concentration performed in a fifth step (circulation/acceleration step).

Then after the circulation step performed for a certain period of time, an acceleration step (fifth step) in the circulation/acceleration step is performed as illustrated in FIG. 10. In the acceleration step, the rotational speed of the second blood pump P2 is controlled to gradually increase the flow rate of plasma. In the working example, the flow rate of plasma is raised from an initial flow rate of 100 ml/min to a rate where platelets start to flow out. This is performed in an acceleration period TG shown in FIG. 19. FIG. 4 illustrates the circulation step and the acceleration step represented by the circulation/acceleration step (S9, S12).

In the acceleration step, the platelets PLT receive ascending force and thereby flow out of the centrifuge bowl E1 through the outflow passage 19, as illustrated in FIG. 3. During the acceleration, no outflow through the outflow passage 19 occurs for the white blood cell layer WBC and the red blood cell layer RBC having large specific densities, thereby receiving greater effect of the centrifugal force.

Figure 20:
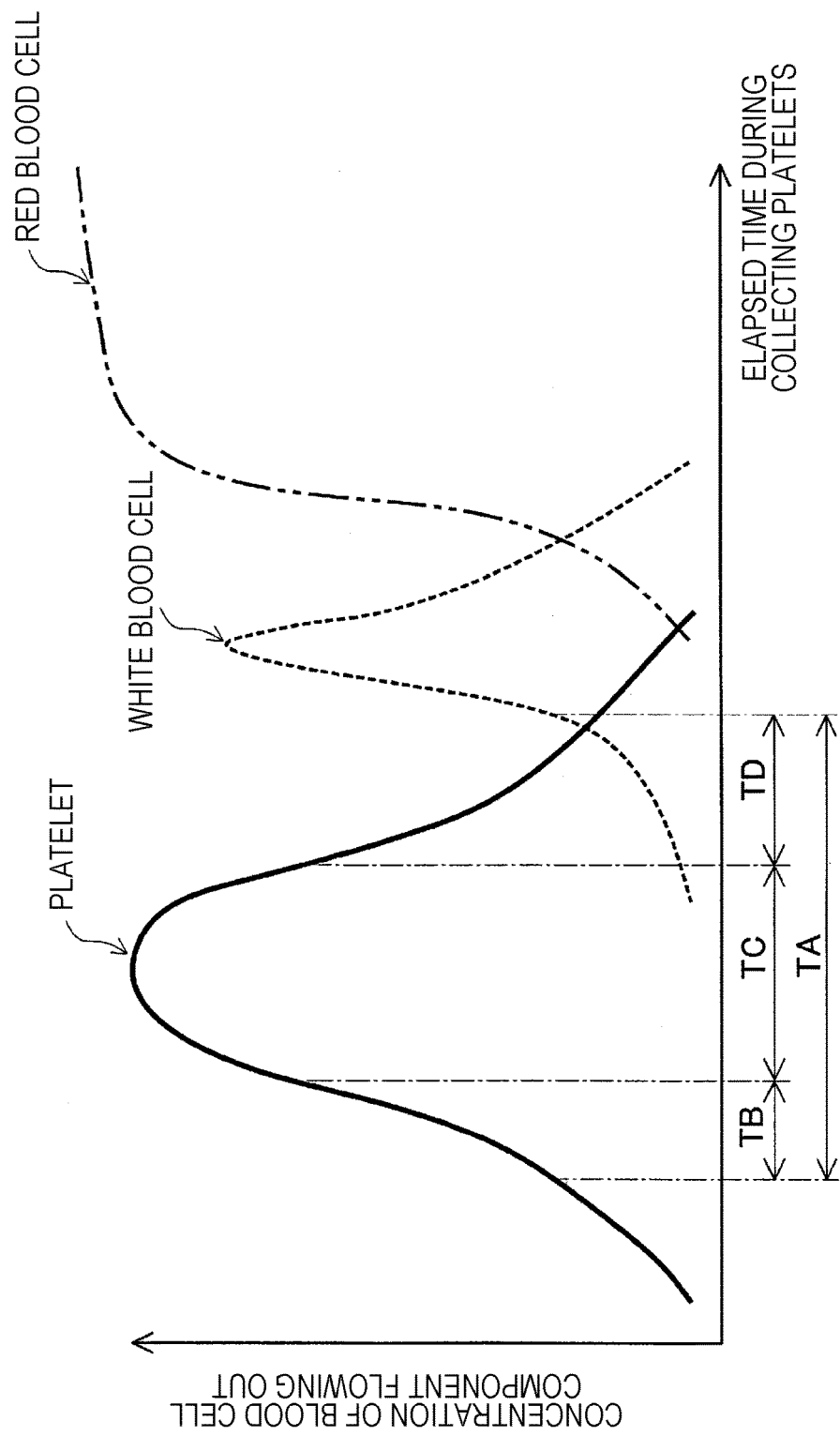
FIG. 20 illustrates changes in concentrations of platelets, white blood cells, and red blood cells flowing out.

FIG. 20 illustrates changes in concentrations of platelets, white blood cells, and red blood cells flowing out. The horizontal axis represents the elapsed time during collecting platelets, and the vertical axis represents concentrations of blood cell components flowing out. First, platelets flow out (outflow period TA). In this period, the outflow rate of platelets gradually increases, and after peaking at the maximum flow rate, the outflow rate gradually decreases. Similarly, the outflow rate of white blood cells gradually increases, and after peaking at the maximum flow rate, the outflow rate gradually decreases.

Figure 5:
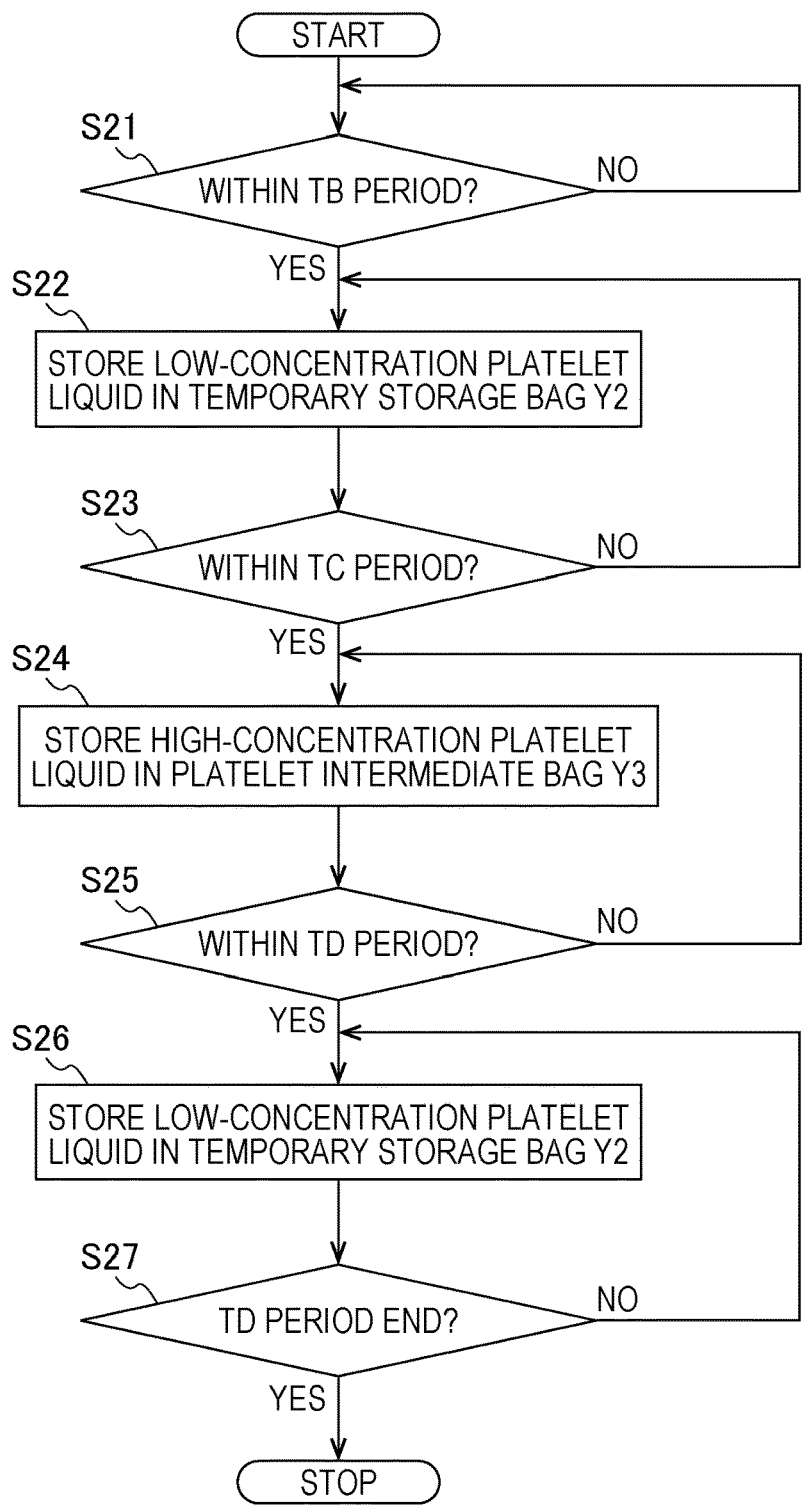
FIG. 5 is a flow chart illustrating an operation performed in a collecting step of platelet liquid.

FIG. 5 illustrates S9 and S12 in detail with a flowchart showing the operation of the blood component separation device.

The outflow period TA of platelets can be divided into periods, namely, a low-concentration period TB coming first in which low-concentration platelet liquid flows out, a high-concentration period TC following the TB period in which high-concentration platelet liquid flows out, and finally a low-concentration period TD in which low-concentration platelet liquid flows out again. Low-concentration platelet liquid is not necessary for obtaining high-concentration platelet liquid.

In the working example, in the acceleration step as illustrated in FIG. 10, when the turbidity sensor C2 detects platelets, that is, when it is determined that the present period is the TB period (S21: YES), the second open/close valve V2 is closed and the fifth open/close valve V5 is opened to store platelet liquid flowing out during the low-concentration period TB in FIG. 20 in the temporary storage bag Y2 (S22). In this state, since the whole blood also flows into the temporary storage bag Y2 and is stored therein, the low-concentration platelet liquid stored in the temporary storage bag Y2 is mixed with the whole blood. Also in this state, the first blood pump P1 is kept operating so that the whole blood drawn from the blood donor is continuously stored in the temporary storage bag Y2.

Note that, the temporary storage bag Y2 is also used as a buffy coat bag as well as a whole blood bag.

Figure 11:
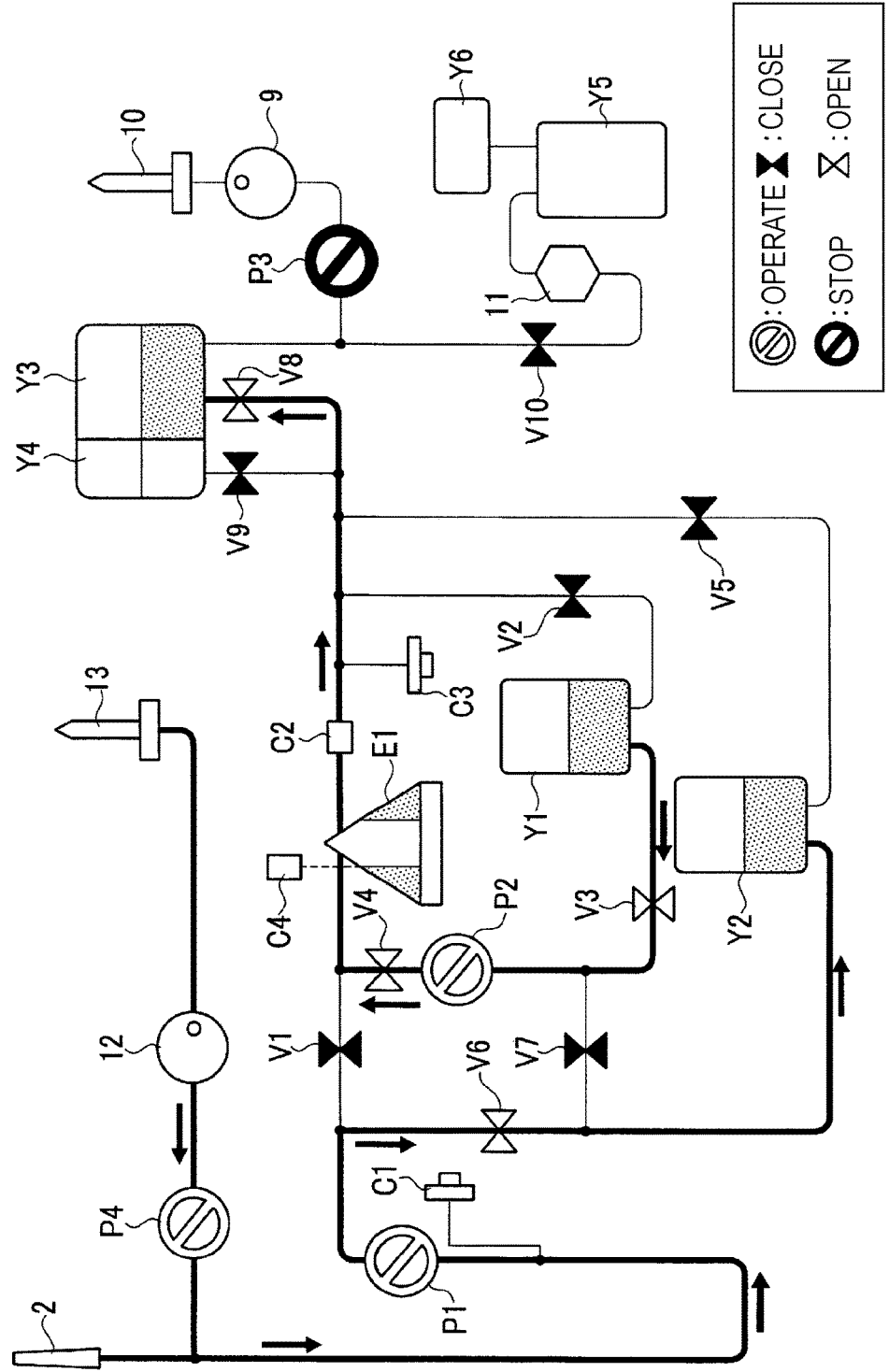
FIG. 11 illustrates a step of storing platelet liquid with high-concentration performed in the fifth step (circulation/acceleration step).

When the turbidity sensor C2 detects that the concentration of platelet liquid is high, it is determined that the present period is the TC period (S23: YES), and the fifth open/close valve V5 is closed and the eighth open/close valve V8 is opened as illustrated in FIG. 11. In this manner, the high-concentration platelet liquid flowing out during the high-concentration period TC can be stored in the platelet intermediate bag Y3 (S24).

If the present cycle is not the last cycle (S7: NO), the first blood pump P1 is kept operating so that the whole blood drawn from the blood donor continuously flows through the sixth open/close valve V6 and is stored in the temporary storage bag Y2.

Figure 12:
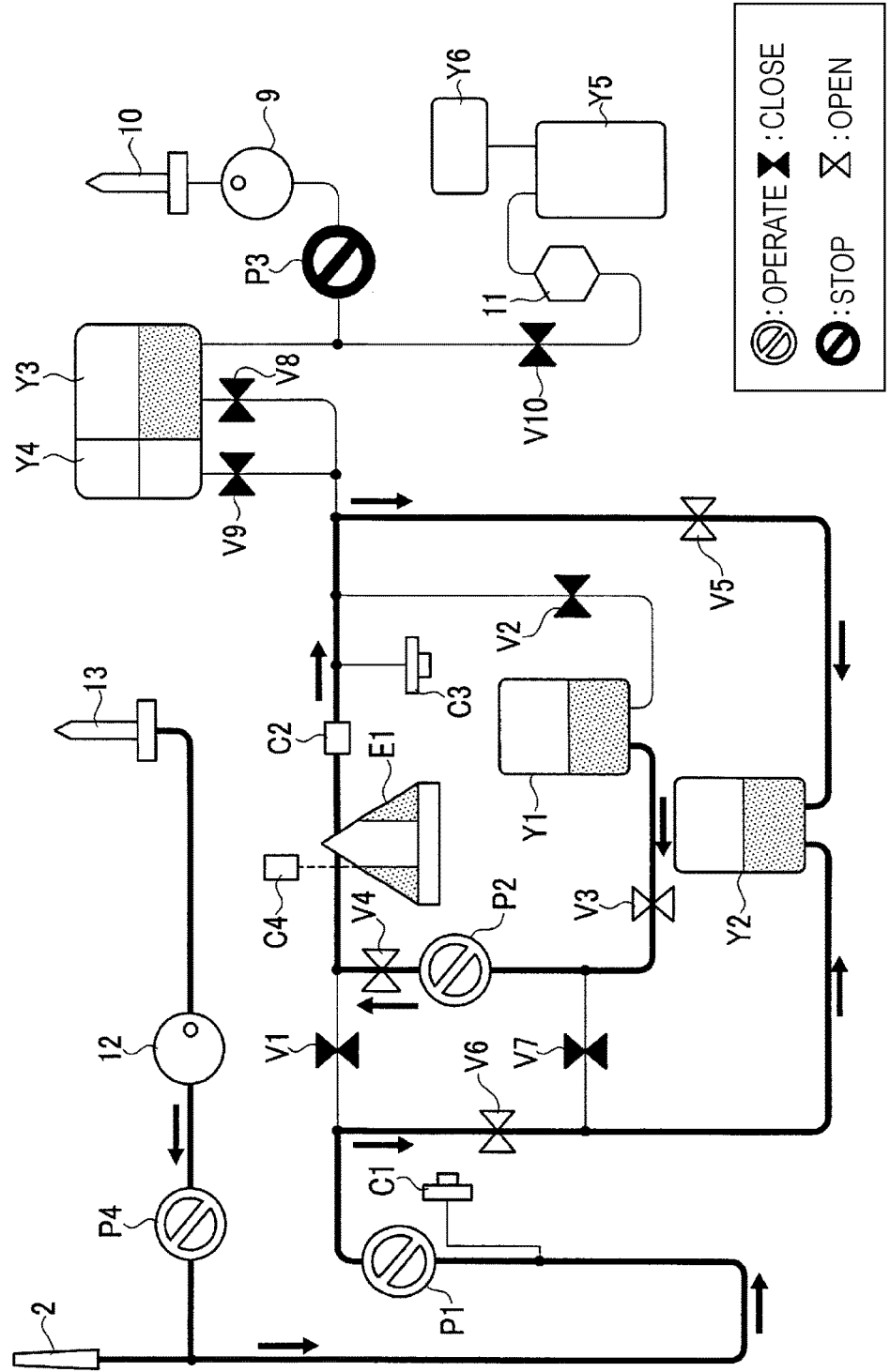
FIG. 12 illustrates a step of collecting platelet liquid with low-concentration performed in the fifth step (circulation/acceleration step).
Figure 13:
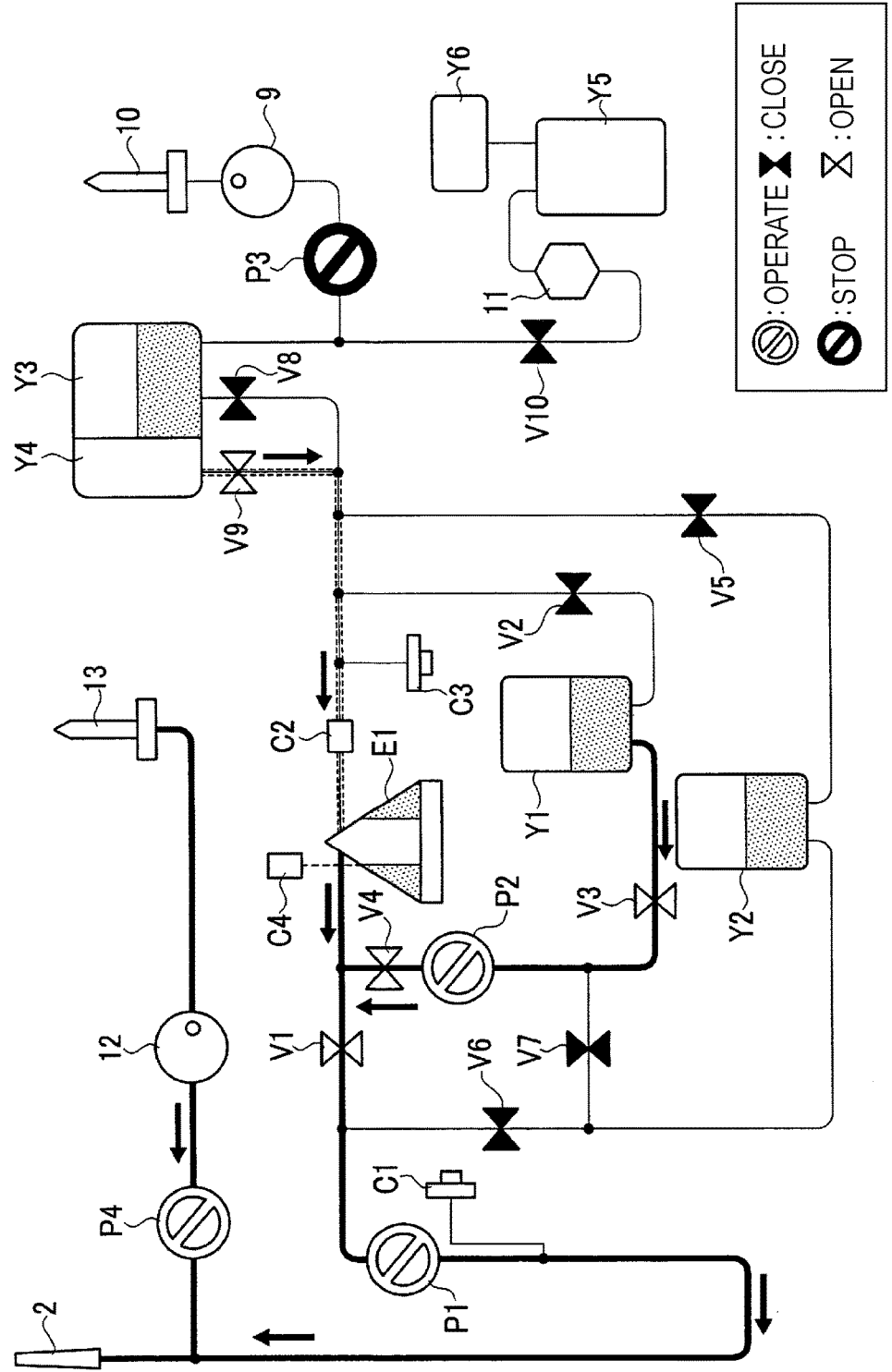
FIG. 13 illustrates a blood returning step.

When the turbidity sensor C2 detects that the turbidity of platelets is below a predetermined value, it is determined that the present period is the TD period (S25: YES), and the eighth open/close valve V8 is closed to block the low-concentration platelet liquid from flowing into the platelet intermediate bag Y3, and the fifth open/close valve V5 is opened, as illustrated in FIG. 12. In this manner, the low-concentration platelet liquid flowing out during the low-concentration period TD can be stored again in the temporary storage bag Y2 (S26).

If the present cycle is not the last cycle (S7: NO), the first blood pump P1 is kept operating so that the whole blood drawn from the blood donor continuously flows through the sixth open/close valve V6 to be stored in the temporary storage bag Y2.

Then when the turbidity sensor C2 detects that the turbidity of platelets is below a predetermined value, it is determined that the TD period is finished (S27: YES), or the outflow of platelets is finished, and the step proceeds to the blood returning step illustrated in FIG. 13 (S10, S13).

In the blood returning step, the centrifuge bowl E1 stops rotation, the sixth open/close valve V6 and the fifth open/close valve V5 are closed, the first open/close valve V1 and the ninth open/close valve V9 are opened, and the first blood pump P1 is reversely rotated, whereby the blood returning starts to return the blood remaining in the centrifuge bowl E1 to the blood donor. The first blood pump P1 is reversely operated with double the rotational speed of the normal rotation to shorten the time of blood returning. Furthermore, as required, the second blood pump P2 is operated to return the excessively collected plasma stored in the plasma bag Y1.

Figure 14:
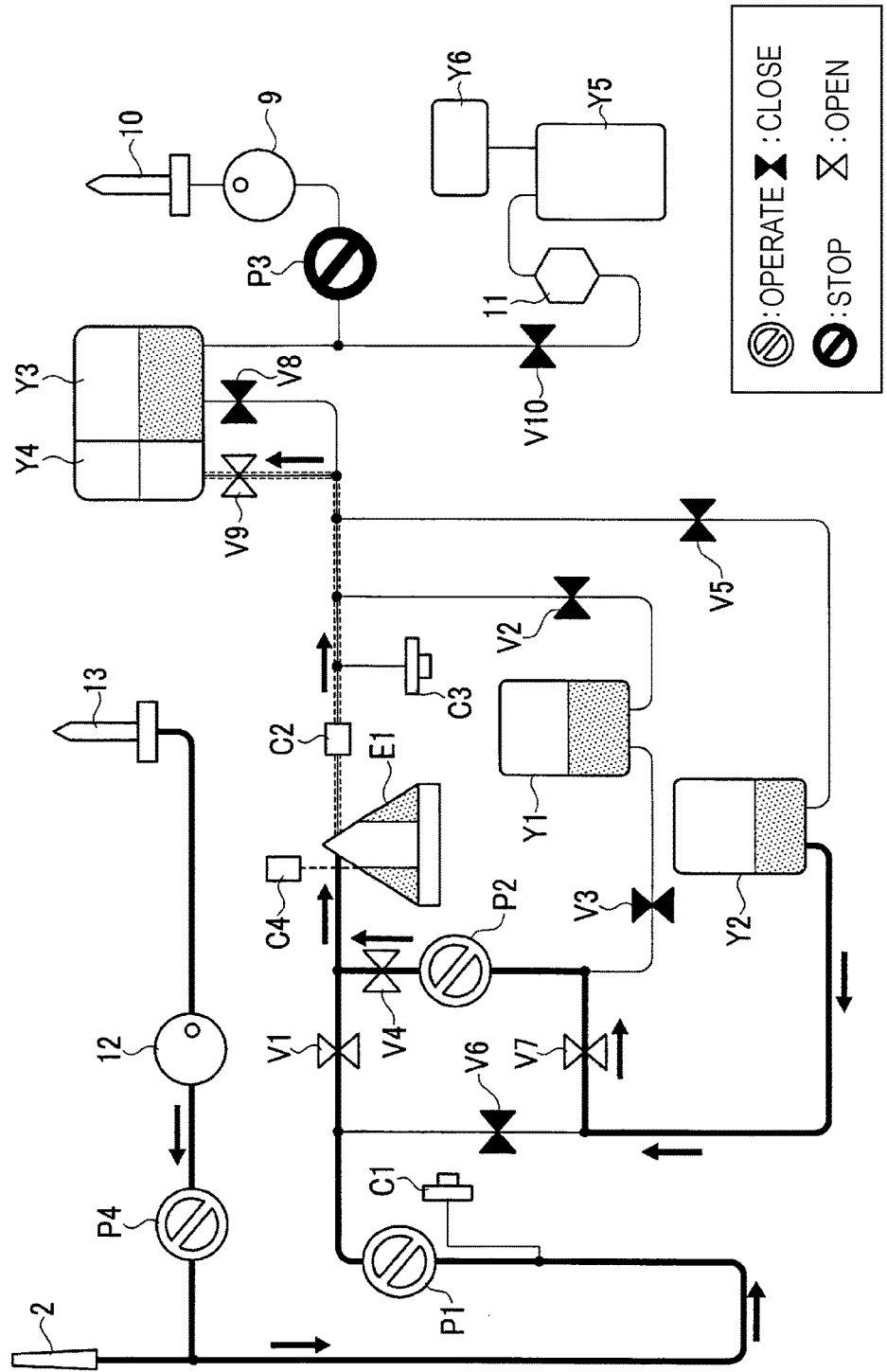
FIG. 14 illustrates the first step performed in a second cycle.

When the blood returning finishes, and if the present cycle is the last cycle (S7: YES), the entire step is finished. When the finished cycle is not the last cycle (S7: NO), the centrifuge bowl E1 starts rotating as illustrated in FIG. 14, and the first blood pump P1 starts normal rotation again to perform blood drawing. The air inside the centrifuge bowl E1 (shown in dashed lines) is pushed by the plasma to flow out through the outflow passage 19 located in the inner periphery of the centrifuge bowl E1. The air then flows through the opened ninth open/close valve V9 and is stored in the air bag Y4. Simultaneously, by opening the seventh open/close valve V7 and operating the second blood pump P2, the blood stored in the temporary storage bag Y2 flows through the fourth open/close valve V4 into the centrifuge bowl E1 (S14). The third open/close valve V3 is closed to block the fluid from flowing into the plasma bag Y1.

Figure 15:
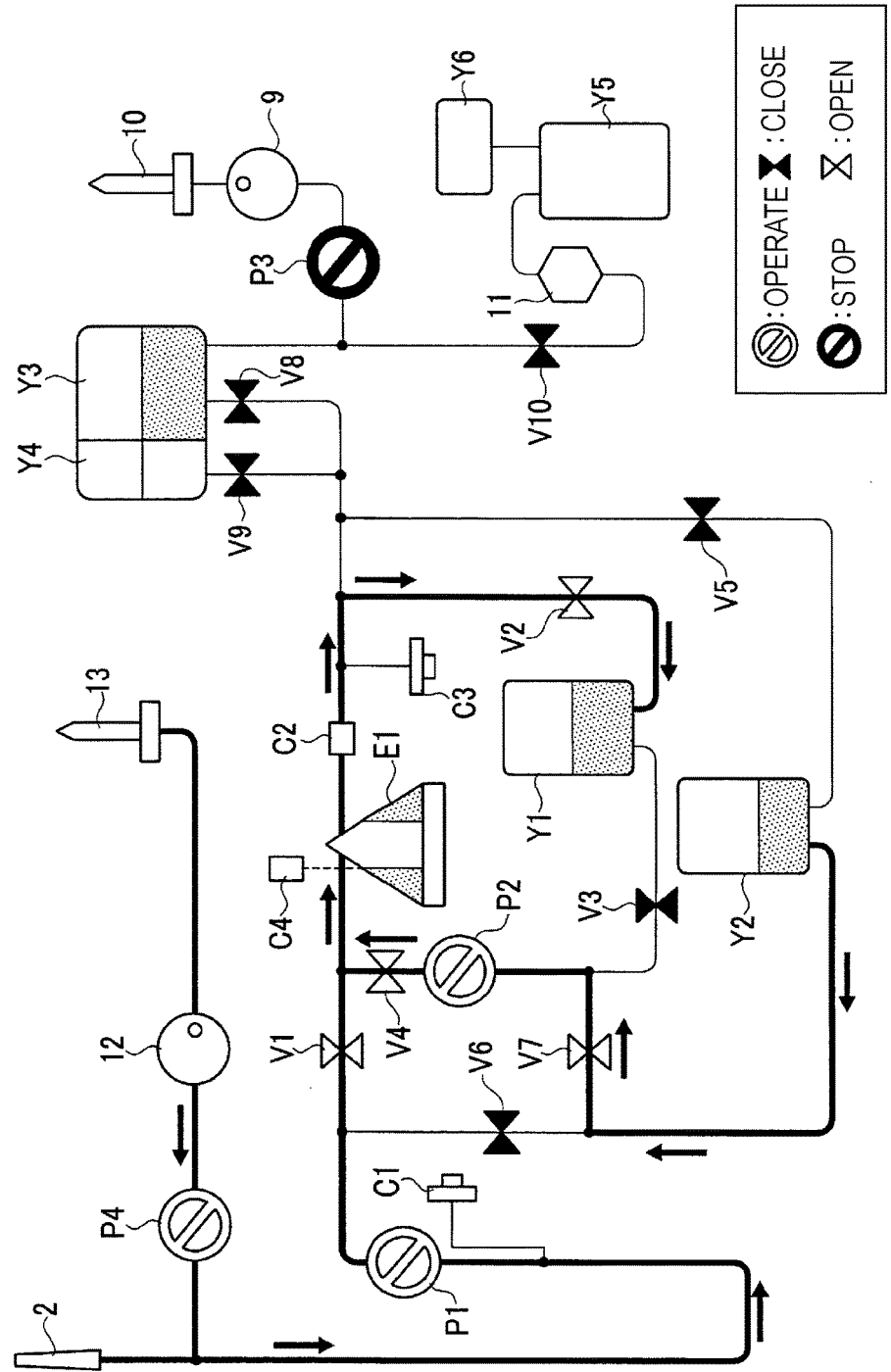
FIG. 15 illustrates the second step performed in the second cycle.

Then when the turbidity sensor C2 detects that the fluid flowing in the tube has changed from air to plasma, the ninth open/close valve V9 is closed and the second open/close valve V2 is opened to store the plasma spilled out from the centrifuge bowl E1 in the plasma bag Y1, as illustrated in FIG. 15.

Figure 16:
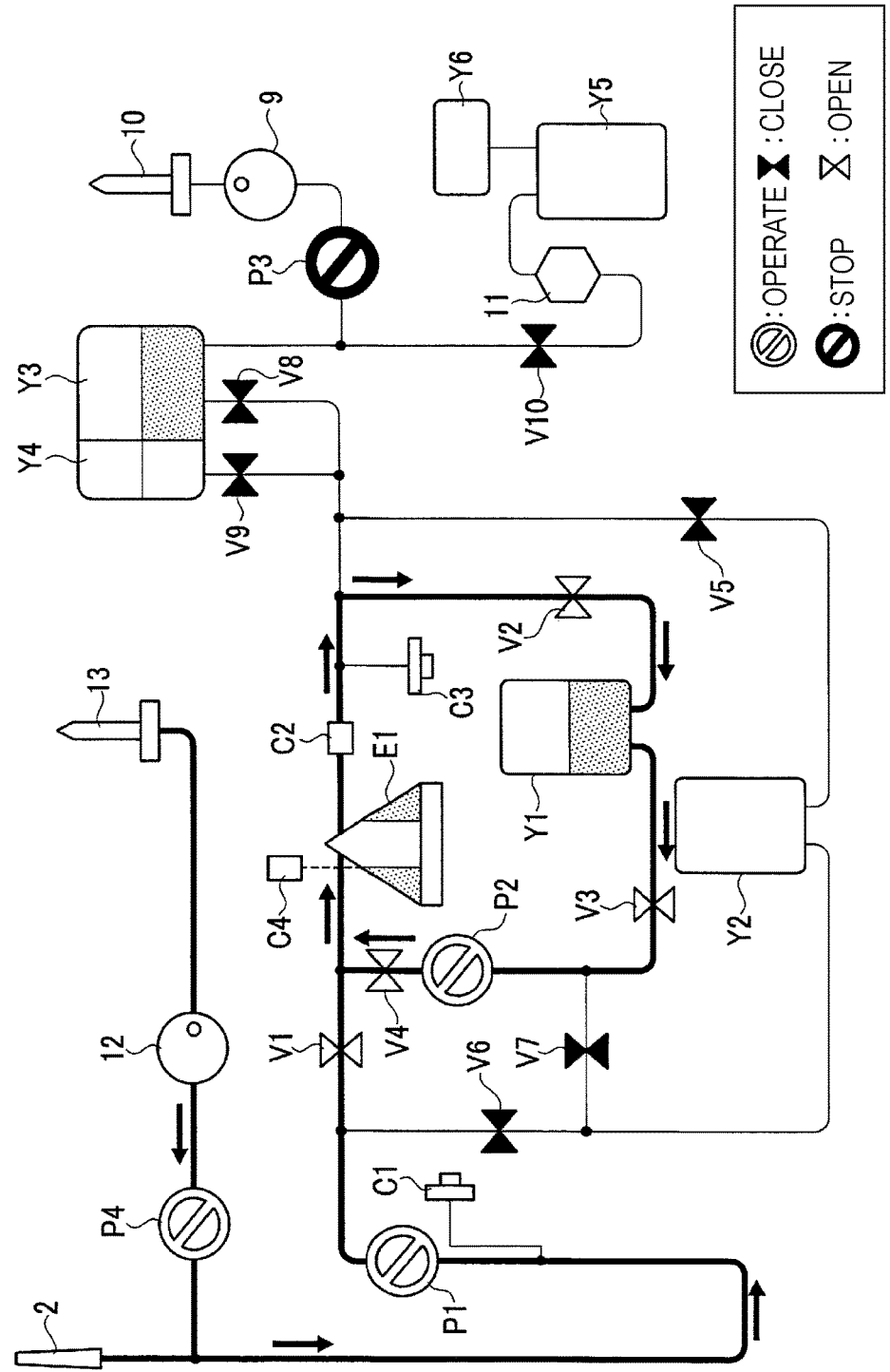
FIG. 16 illustrates the third step performed in the second cycle.

Then when it is confirmed that all the blood in the temporary storage bag Y2 has returned to the centrifuge bowl E1 and that a predetermined amount of plasma is stored in the plasma bag Y1 (S4: YES), the seventh open/close valve V7 is closed with the second blood pump P2 kept operating, and the third open/close valve V3 is opened to mix the plasma stored in the plasma bag Y1 with whole blood and to supply the mixture of the plasma and the whole blood to the centrifuge bowl E1, whereby the critical flow step of plasma is started, as illustrated in FIG. 16 (a state same as in FIG. 8). The step proceeds to the step illustrated in FIG. 9 (circulation step).

This cycle is repeated, typically three or four times, until a predetermined amount of platelets PLT is obtained. When the operation is to finish after three cycles, the blood drawing is performed in parallel with the circulation period TF2 and the acceleration period TG2 in the second cycle to store whole blood in the temporary storage bag Y2. Then during blood drawing in the third cycle, the blood in the temporary storage bag Y2 is mixed with whole blood and supplied to the centrifuge bowl E1. Furthermore, during the circulation period TF3 and the acceleration period TG3 in the third cycle, blood drawing is not performed. This is because there is no fourth cycle.

When the operation is to finish after three cycles, the blood drawing needle 2 is removed from the blood donor after blood returning in the third cycle, thereby finishing the blood drawing. The ACD pump P4 is stopped to stop supplying of ACD liquid to the donor tube T1.

Figure 17:
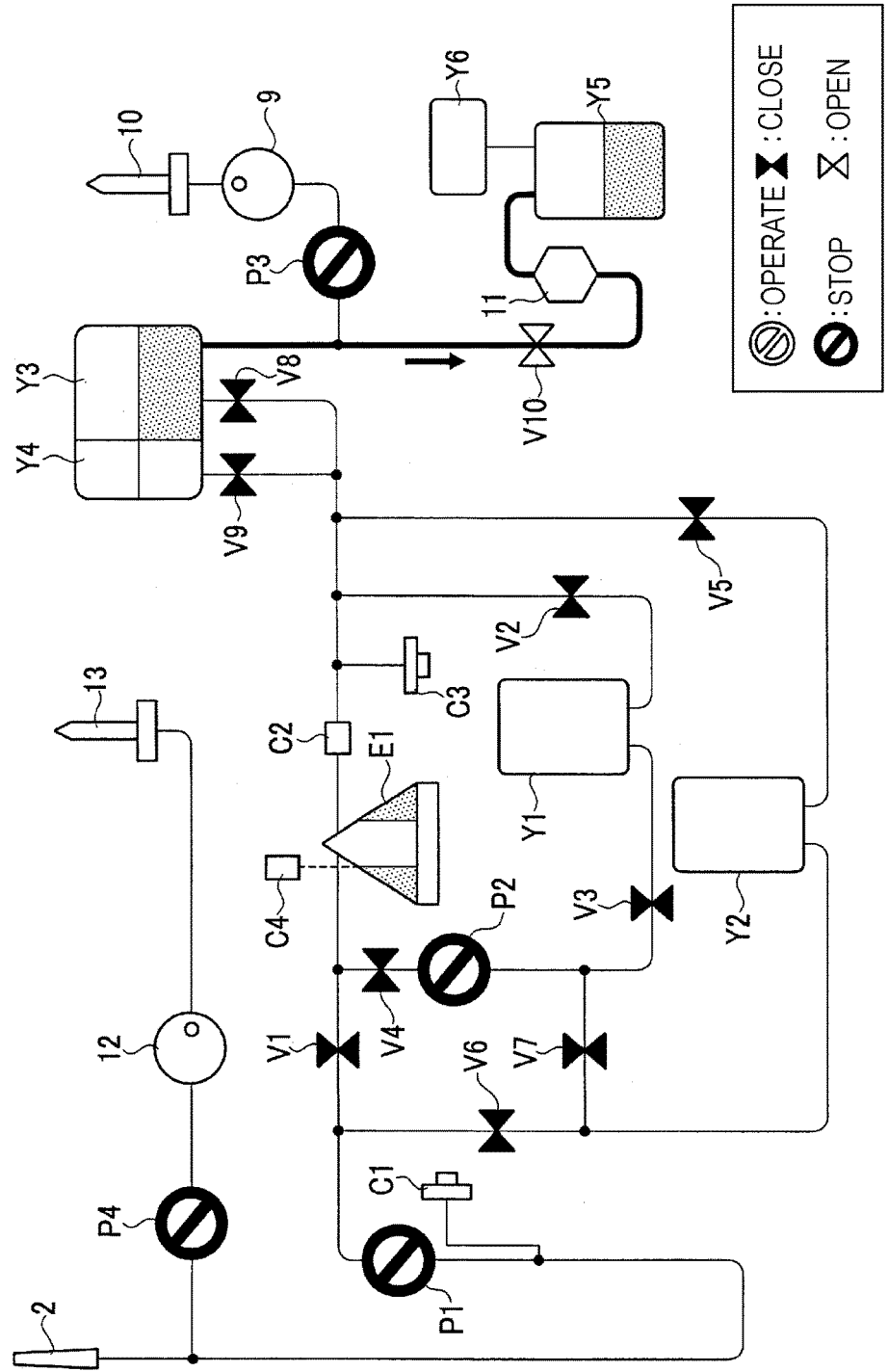
FIG. 17 illustrates a processing step of platelet liquid.

Then the third blood pump P3 is operated to inject a suitable amount of Platelet additive solution into the platelet intermediate bag Y3 through a bottle needle 10 coupled to the Platelet additive solution bottle. As illustrated in FIG. 17, the tenth open/close valve V10 is then opened to inject the high-concentration fourth platelet liquid stored in the platelet intermediate bag Y3 into the platelet bag Y5 through the white blood cell removal filter 11. In this process, the air in the platelet bag Y5 moves into the air bag Y6.

Figure 18:
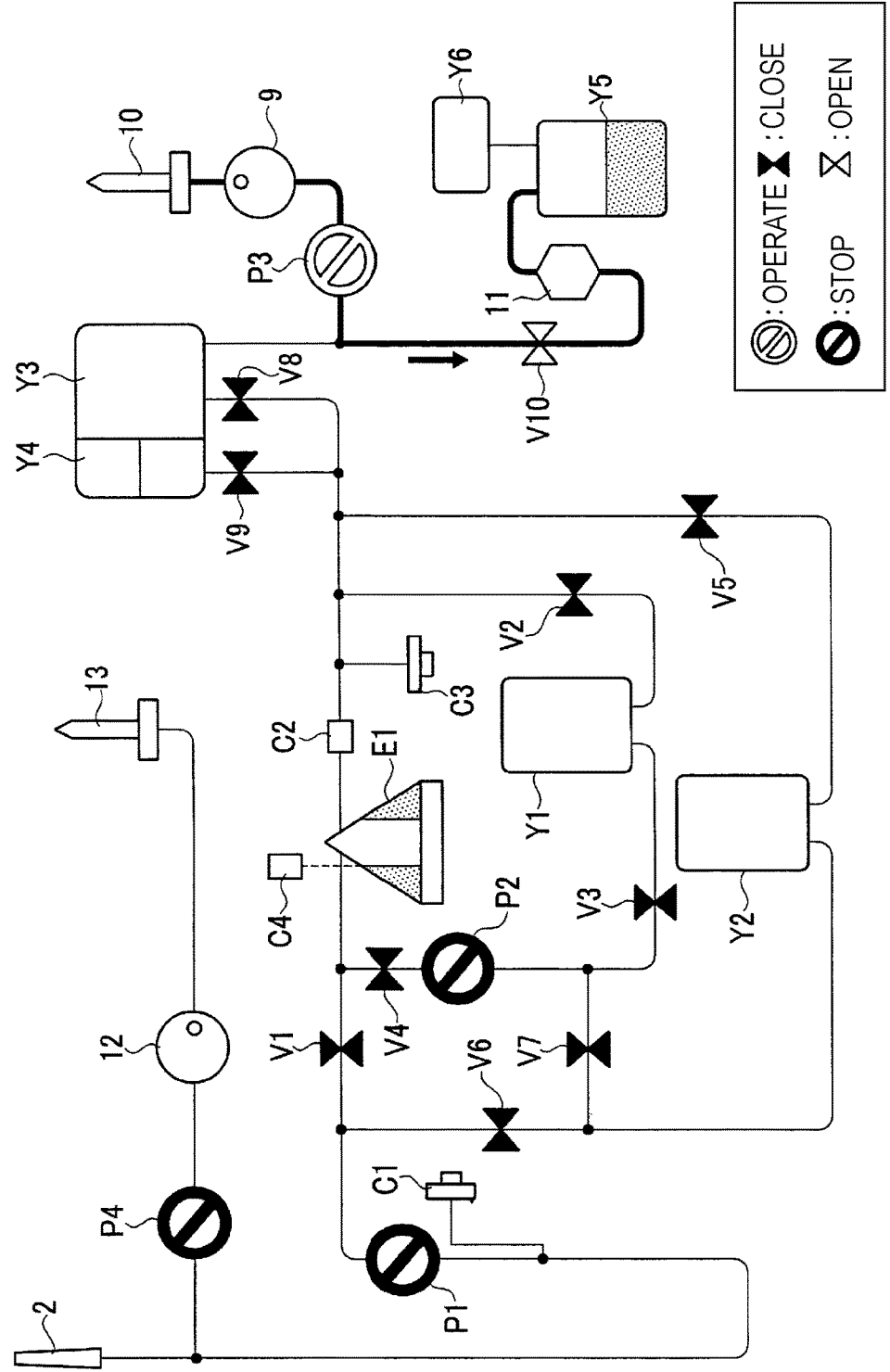
FIG. 18 illustrates a final processing step of platelet liquid.
Figure 19:
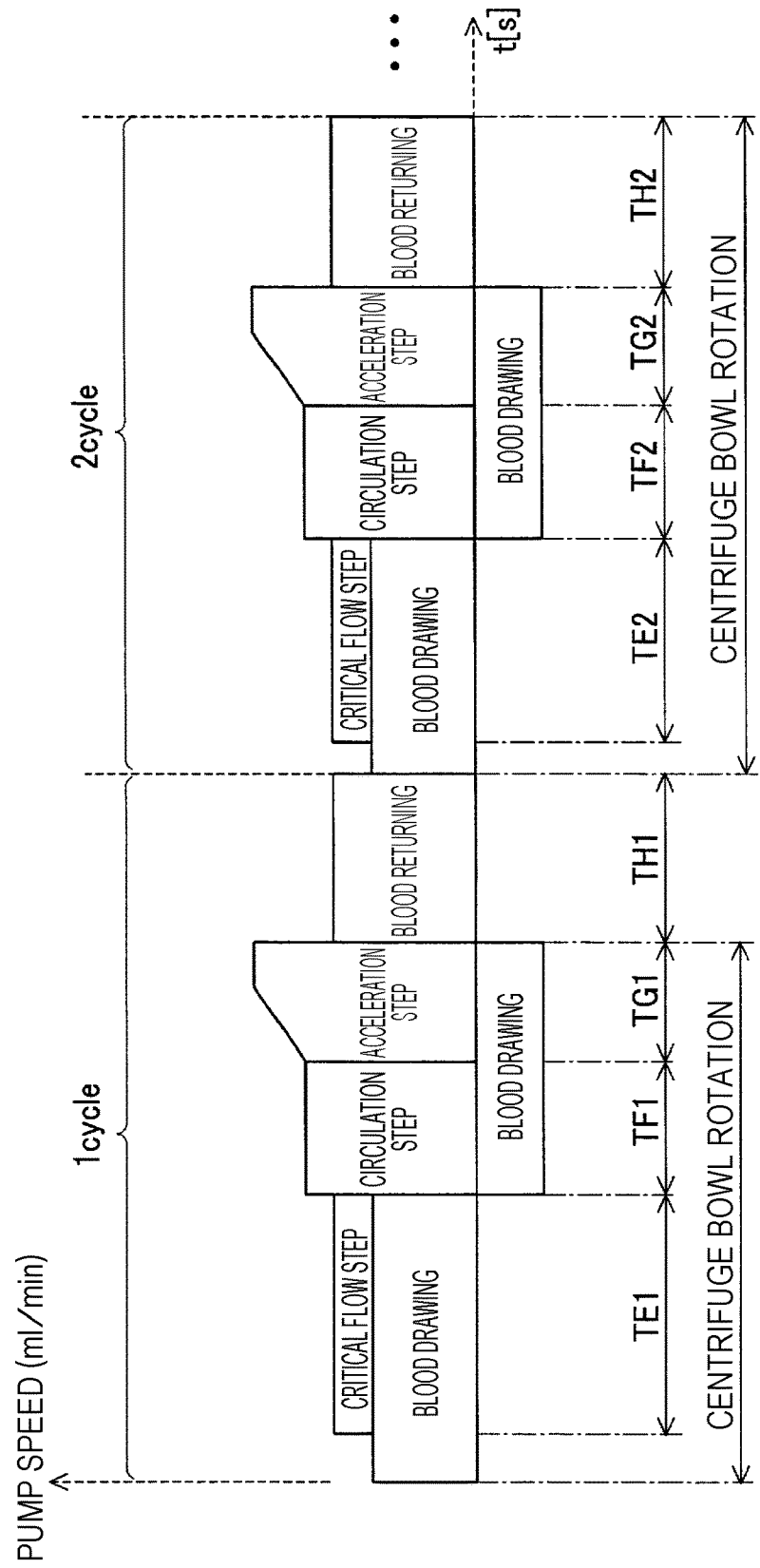
FIG. 19 illustrates an operation of the blood component separation device in chronological order.

After confirming that the high-concentration platelet liquid stored in the platelet intermediate bag Y3 has completely been taken out, the third blood pump P3 is operated to inject the Platelet additive solution remaining in the Platelet additive solution bottle into the platelet bag Y5, through the sterilizing filter 9 and the white blood cell removal filter 11, through the bottle needle 10 coupled to the Platelet additive solution bottle, as illustrated in FIG. 18. In this manner, the high-concentration platelet liquid, which is already filtered, remaining on the white blood cell removal filter 11 is collected. Then two tubes of the platelet bag are sealed. In this manner, the platelet bag Y5 storing high-concentration platelet liquid is prepared.

The supplied amount of ACD liquid to prevent coagulation of blood is now described. In the working example, a certain amount (for example, 30 ml) of ACD liquid is supplied to the centrifuge bowl E1 through the first open/close valve V1 in the priming step (step S1 in FIG. 4), and during the drawing of whole blood (step S2 in FIG. 4), the continuously supplied ACD liquid is mixed with whole blood and the whole blood is supplied to the centrifuge bowl E1.

For example, when a same amount of ACD liquid is supplied to blood donors (donors), the concentration of ACD in platelet liquid (ACD liquid concentration) stored in the platelet intermediate bag Y3 varies among blood donors having different HCT values, as shown in FIG. 21. For example, as illustrated in FIG. 21, if the HCT value of the blood donor ranges from 36.9% to 47.0%, the ACD concentration in platelet liquid varies from 17.6% to 20.0% under the same amount of ACD liquid supplied.

Such variation in the ACD concentration in platelet liquid among blood donors depending on the HCT value may be understood as will be explained below. First, for a low HCT value, an amount of components other than red blood cells, such as plasma and platelets, is large, and for a high HCT value, an amount of components other than red blood cells, such as plasma and platelets, is small. Hence, if a same amount of ACD liquid is supplied regardless of the HCT value, the ACD concentration in platelet liquid becomes low for a low HCT value representing a large amount of platelet liquid, and the ACD concentration in platelet liquid becomes high for a high HCT value representing a small amount of platelet liquid.

Figure 22:
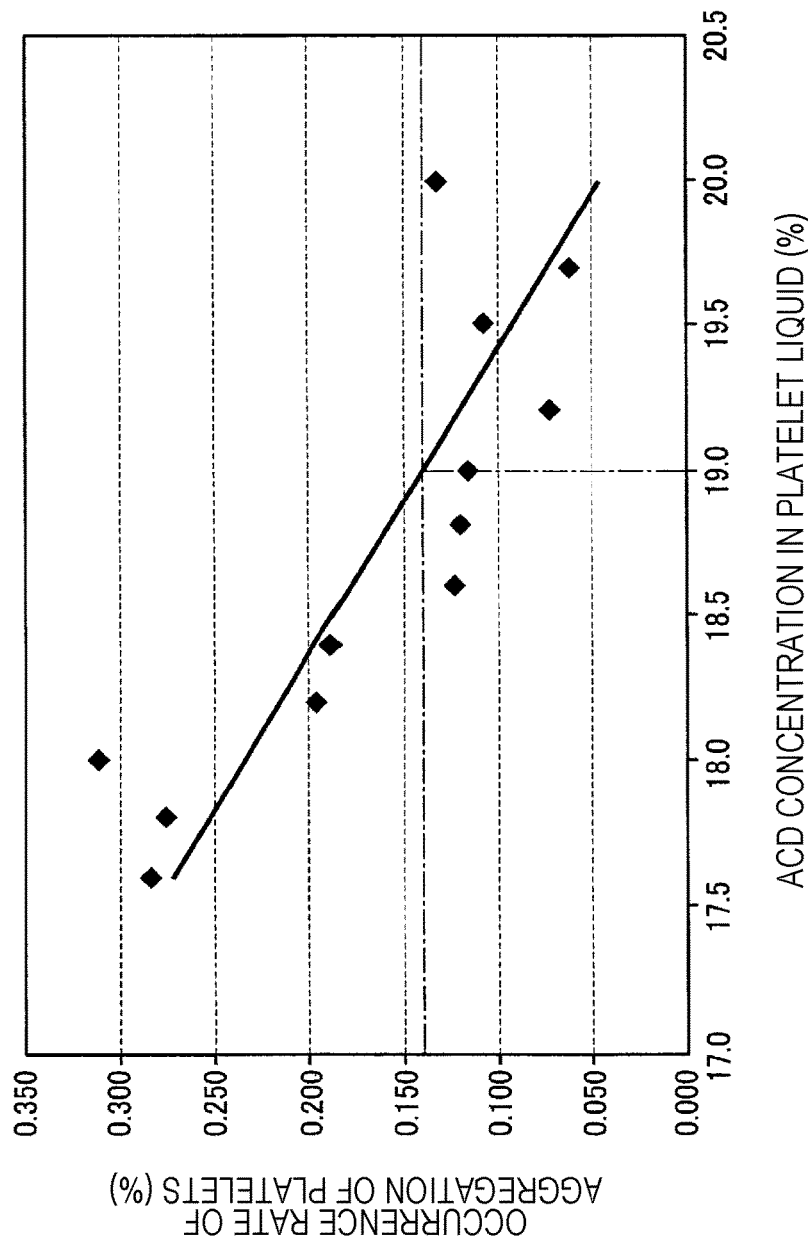
FIG. 22 is a chart illustrating the relation between ACD concentration in platelet liquid and the rate of occurrence of aggregation of platelets.

As illustrated in FIGS. 21 and 22, the relationship between the ACD concentration in platelet liquid and aggregation of platelets is recognized from the accumulated data. The rate of occurrence of platelet aggregation is high for a low ACD concentration in platelet liquid. When the rate of occurrence of platelet aggregation is high, the number of platelets in the collected platelet liquid might be lower than a targeted specification for pharmaceutical preparation (causing unit shortage).

In the working example, as illustrated in FIG. 23, the ACD ratio, or a ratio of the amount of the ACD liquid in relation to the blood, is set according to the HCT value of a blood donor so as the ACD concentration in platelet liquid stored in the platelet intermediate bag Y3 to be at a predetermined value (for example, 190).

Specifically, the ACD ratio (amount of the ACD liquid in relation to the blood) is set higher for a low HCT value, and the ACD ratio is set lower for a high HCT value. More specifically, based on the HCT value which is input to the blood component separation device, the ACD ratio is determined according to FIG. 23, and the ACD liquid is supplied by the amount determined by the ACD ratio. During the continuous supply of ACD liquid after the start of the drawing of whole blood (step S2 in FIG. 4), the amount of the ACD liquid to be supplied is determined by subtracting the amount of ACD liquid already supplied (for example, 30 ml) in the priming step (step S1 in FIG. 4) from the whole amount of ACD liquid to be supplied which is calculated from the ACD ratio.

In the example illustrated in FIG. 23, the ACD ratio is set higher for a lower HCT value when the HCT value is within the range from 34% to 43%, and the ACD ratio is set constant when the HCT value is within the range from 43% to 52%.

As illustrated in FIG. 23, when the HCT value is, for example, 34%, the ACD ratio, or the ratio of the amount of ACD liquid to the amount of blood, is set to 1:7.8, and when the HCT value is, for example, 50%, the ACD ratio, or the ratio of the amount of ACD liquid to the amount of blood, is set to 1:9.0. As a result, the ACD concentration in platelet liquid stored in the platelet intermediate bag Y3 is set to 19%, regardless of the HCT value. Then the rate of occurrence of aggregation of platelets is set to 0.14% or lower as shown in FIG. 22, and the aggregation of platelets can be minimized.

In the embodiment, the ACD ratio is set according to the HCT value of a blood donor so that the ACD concentration in platelet liquid is controlled to a value which minimizes the rate of occurrence of aggregation of platelets. The relationship between the HCT value and the ACD ratio may be determined by a map as illustrated in FIG. 23, or may be determined by formulas.

According to the first working example as described above, in the blood component separation device that separates platelet liquid from the blood drawn from a blood donor while supplying to the blood ACD liquid for preventing coagulation of the blood, the ACD ratio, or a ratio of the amount of the ACD liquid supplied in relation to the blood, is set according to the HCT value of the blood donor so that the ACD concentration in the separated platelet liquid becomes a predetermined value (for example, 19%). In this manner, when the platelet liquid is separated from the blood, the ACD concentration in the platelet liquid separated and collected can be kept constant. The ratio of occurrence of the aggregation of platelets can thus be minimized. As a result, a pharmaceutical preparation of platelet liquid that conforms to the targeted specification for pharmaceutical preparation can be obtained.

The blood component separation device performs the priming step of supplying ACD liquid, before blood drawing, to the centrifuge bowl E1. The amount of the ACD liquid to be supplied determined by the ACD ratio includes the amount of the ACD liquid supplied in the priming step. So that the ACD liquid can surely be applied to the portion that makes contact with blood in the priming step performed before blood drawing, thereby preventing coagulation in blood when introduced.

The blood component separation device performs (a) centrifugal separation step, (b) circulation flow step, (c) circulation/acceleration step, and (d) blood returning step. Steps (a) to (d) constitute one cycle, and the blood component separation device performs a plurality of cycles. In this manner, the platelet liquid can accurately be separated from other blood components. Moreover, since the timing of collecting platelet liquid with high-concentration is optimized, further larger amount of platelet can efficiently be collected.

Furthermore, the circulation/acceleration step performed by the blood component separation device includes a first collecting step of transferring a portion of platelet liquid with low-concentration to a temporary storage bag Y2 and a second collecting step of collecting a portion of platelet liquid with high-concentration. The platelet liquid with low-concentration transferred to the temporary storage bag Y2 is introduced into the centrifuge bowl E1 together with the whole blood drawn in the following cycle. This process can be used for BC (buffy coat) recycling to obtain platelet liquid with high-concentration, and thereby further larger amount of platelet can be collected.

Second Working Example

Figure 24:
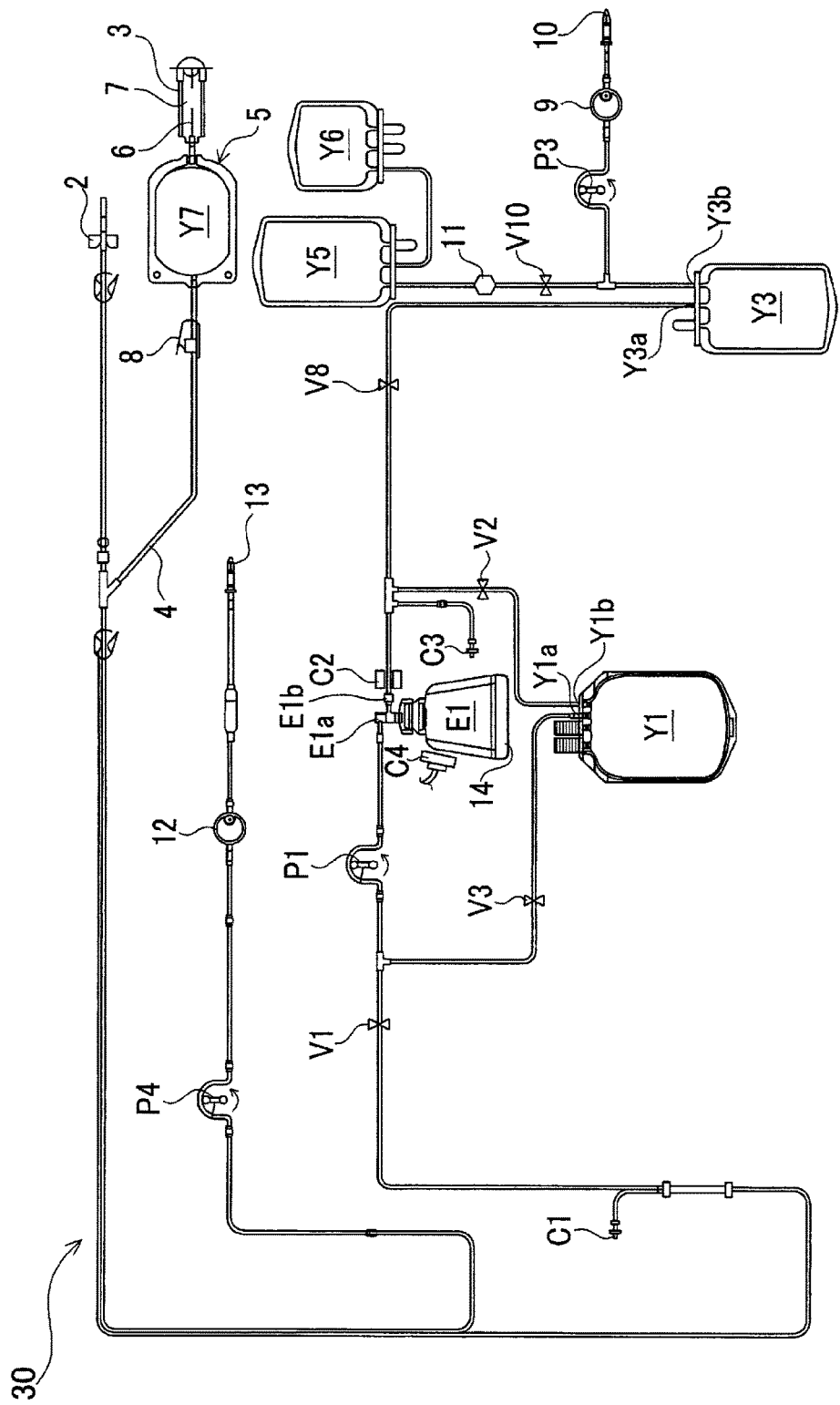
FIG. 24 illustrates a configuration of a blood component separation device according to a second working example.

Now, a second working example will be described. The component similar to that of the first working example is appended with the same reference sign and the description thereof will be omitted. Description will mainly be made for the difference between the second working example and the first working example. The major difference between the blood component separation device according to the second working example and the blood component separation device of the first working example is that the second working example does not employ BC recycling. FIG. 24 illustrates a system configuration of a blood component separation device according to the second working example. The major difference between the blood component separation circuit 30 according to the second working example and the first working example is that the second working example does not include the temporary storage bag Y2.

Figure 25:
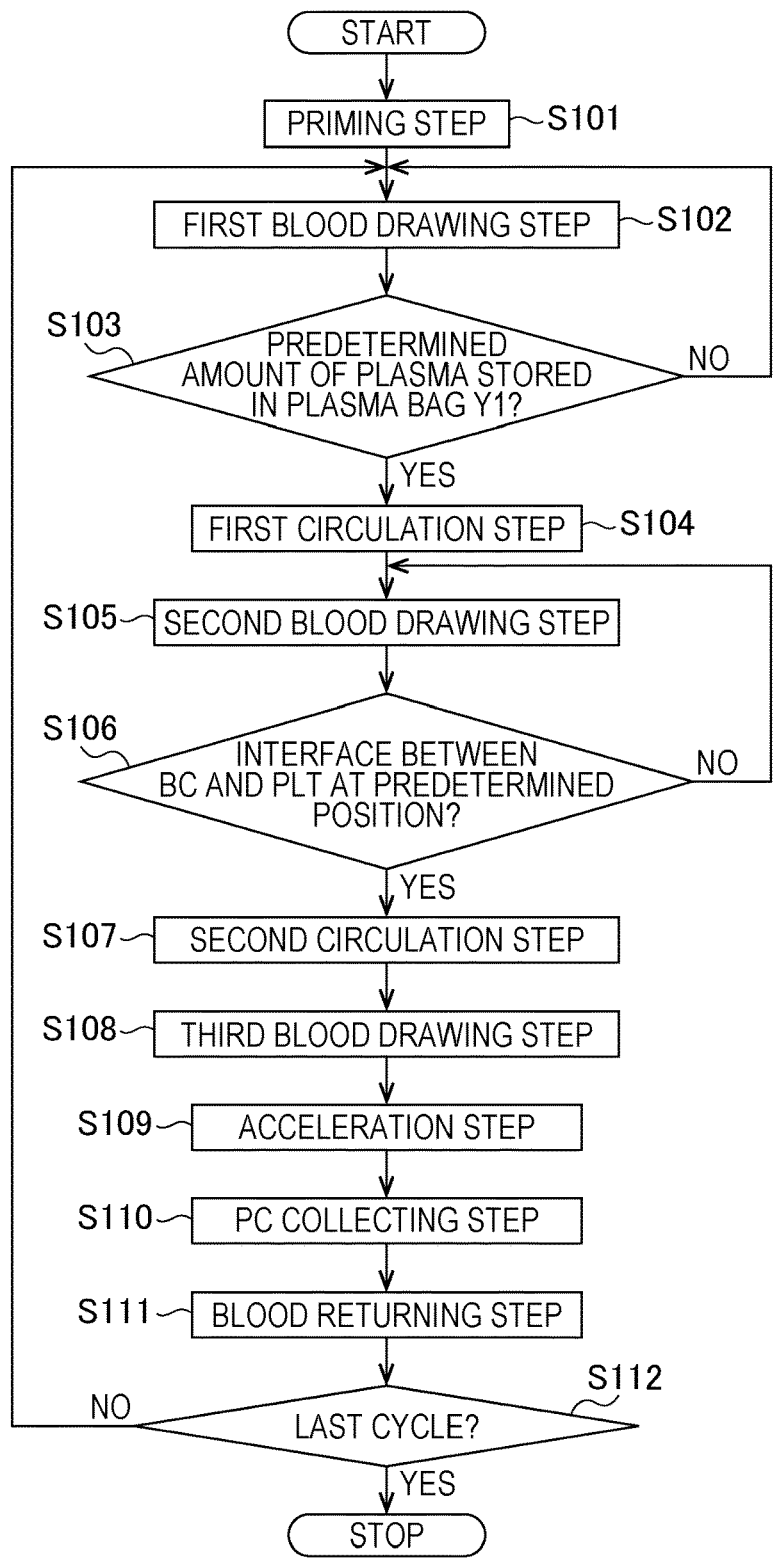
FIG. 25 is a flow chart illustrating an operation of the blood component separation device according to the second working example.
Figure 26:
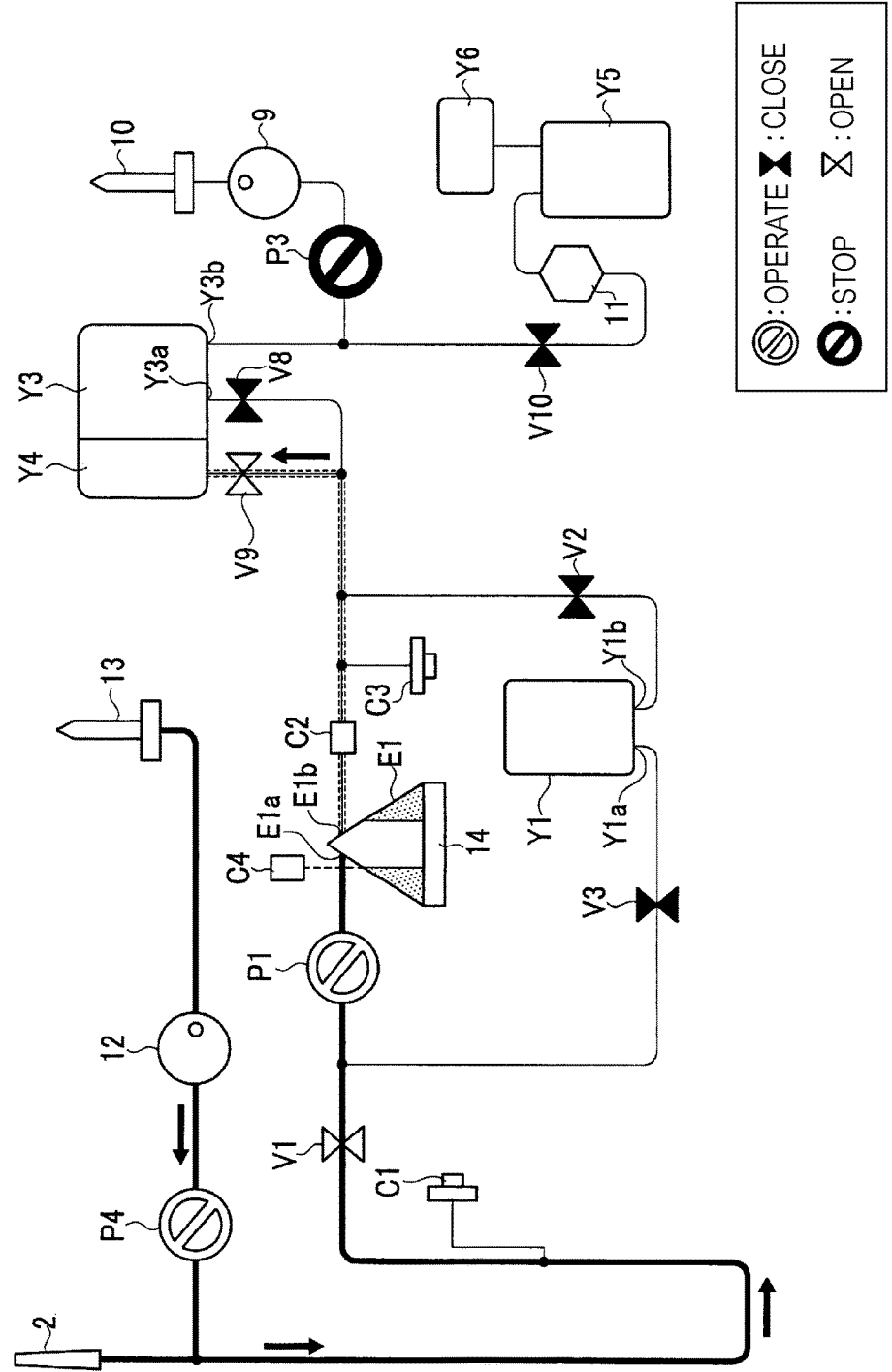
FIG. 26 illustrates a blood drawing step of the blood component separation device according to the second working example.
Figure 27:
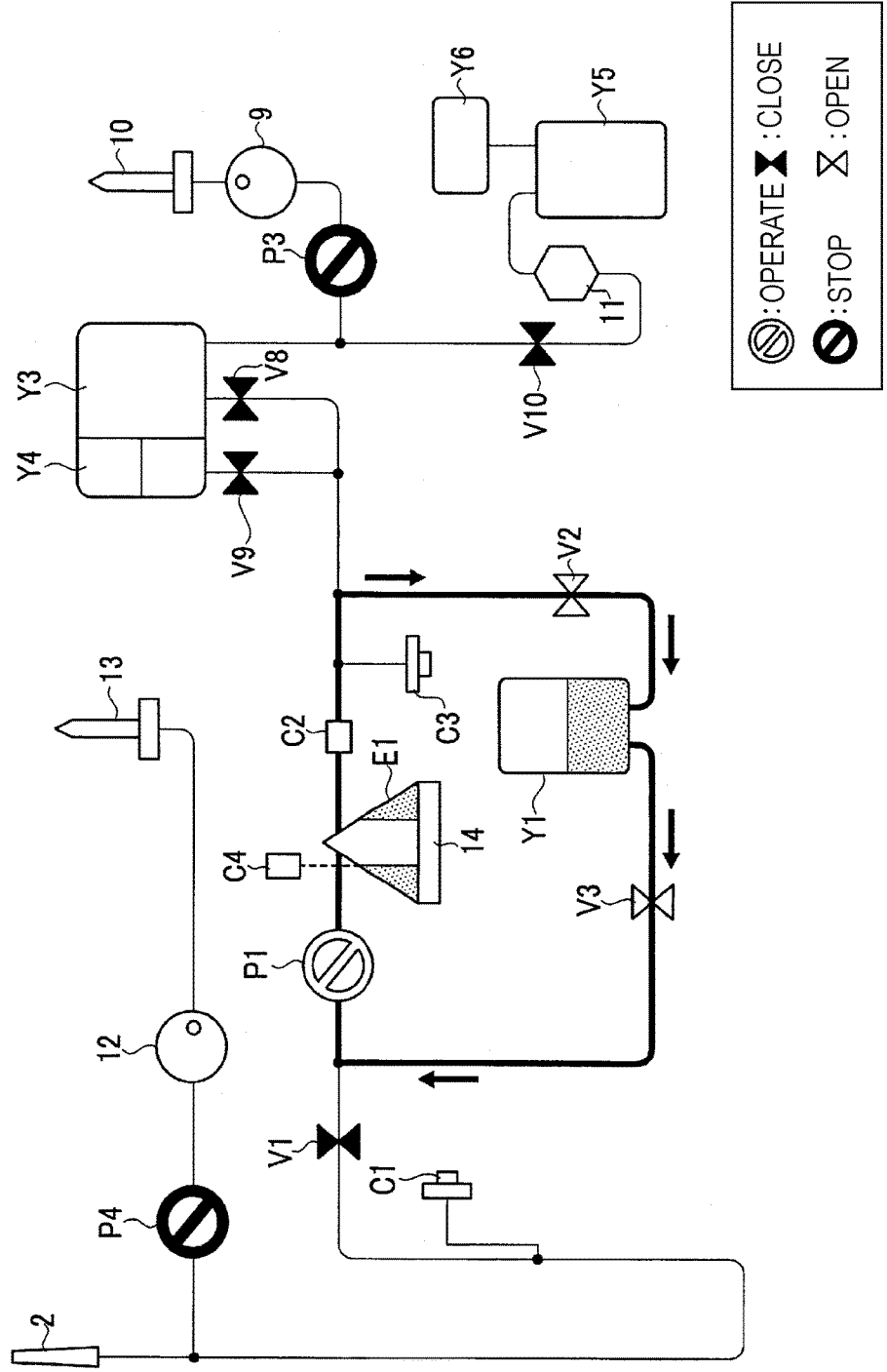
FIG. 27 illustrates a circulation step of the blood component separation device according to the second working example.
Figure 28:
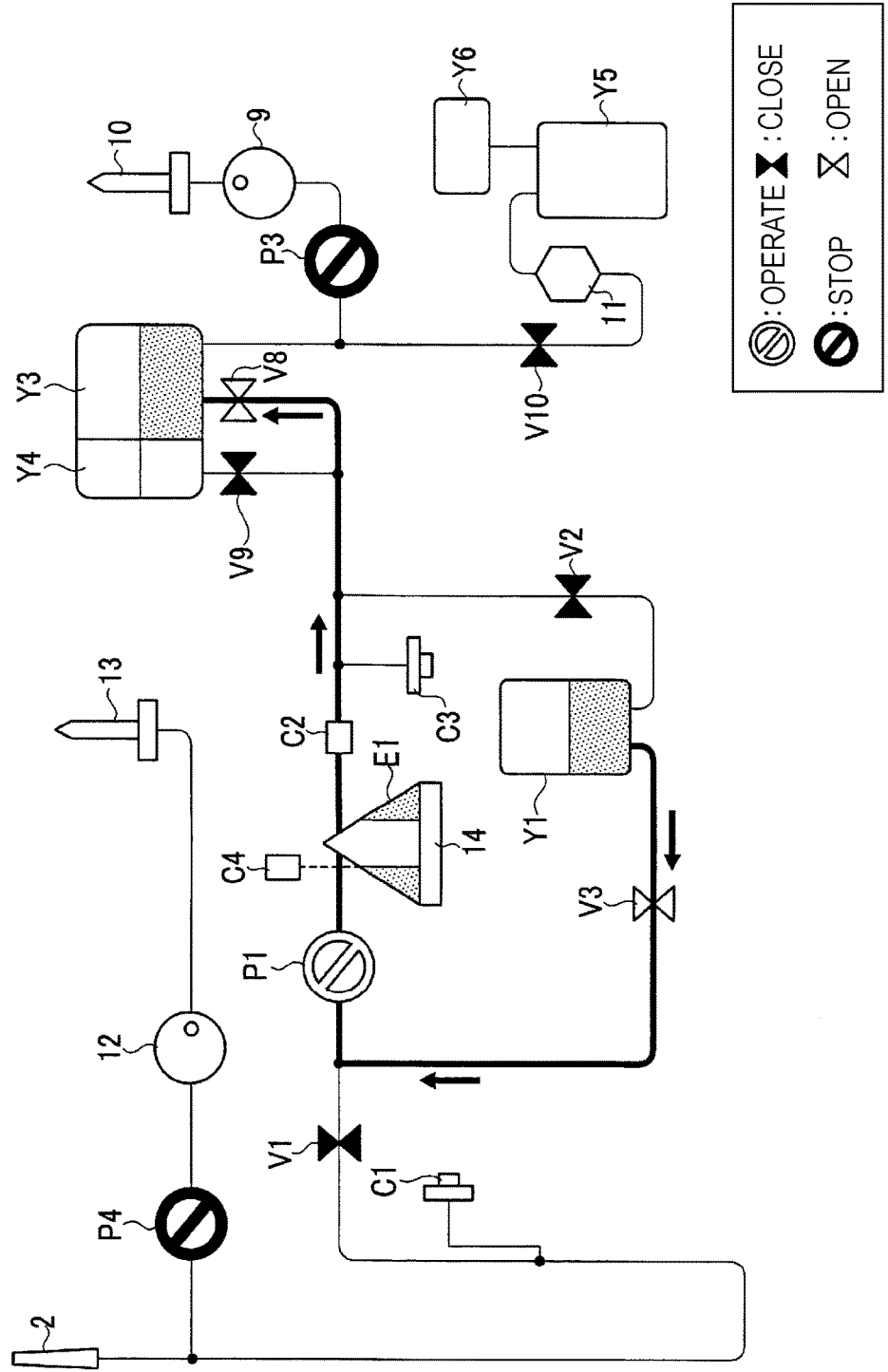
FIG. 28 illustrates a PC collecting step of the blood component separation device according to the second working example.

The operation of the blood component separation device according to the second working example will be described. FIG. 25 is a flow chart illustrating the operation of the blood component separation device. The operation and steps performed in the blood component separation device are illustrated in FIGS. 26 to 28.

Similarly to the first working example, the blood component separation device according to the second working example first performs a priming step (S101). At the same time, as illustrated in FIG. 26, the drawing of whole blood and centrifugal separation start (S102: first blood drawing step). As in the same manner as the priming step, the ACD pump P4 is operated to supply ACD liquid to the donor tube T1 so that the ACD liquid is mixed with the whole blood, which is then supplied to the centrifuge bowl E1. Then the ninth open/close valve V9 is closed and the second open/close valve V2 is opened to store the plasma spilled out from the centrifuge bowl E1 in the plasma bag Y1.

When a certain amount of plasma is stored in the plasma bag Y1 (S103: YES), as illustrated in FIG. 27, the first open/close valve V1 is closed to temporarily stop the drawing of whole blood, and the third open/close valve V3 is opened to return the plasma into the centrifuge bowl E1 (S104: first circulation step).

Then the first open/close valve V1 is opened to restart drawing of whole blood to introduce the blood into the centrifuge bowl E1 (S105: second blood drawing step). In this process, similarly to the first blood drawing step, the ACD pump P4 is operated to supply ACD liquid to the donor tube T1 so that the ACD liquid is mixed with the whole blood, which is then supplied to the centrifuge bowl E1.

When the interface sensor C4 detects that the interface between the buffy coat layer BC and the red blood cell layer RBC in FIG. 3 has come to a predetermined position (S106: YES), similarly to the first circulation step, the first open/close valve V1 is closed to temporarily stop the drawing of whole blood, and the third open/close valve V3 is opened to return the plasma into the centrifuge bowl E1 (S107: second circulation step). The circulation speed is raised from 60 ml/min to as high as 170 to 200 ml/min.

The first open/close valve V1 is opened to restart drawing of whole blood. The amount of whole blood to be drawn is automatically calculated according to the HCT value so that collection of platelets can surely be performed (S108: third blood drawing step). In this process, similarly to the first blood drawing step and the second blood drawing step, the ACD pump P4 is operated to supply ACD liquid to the donor tube T1 so that the ACD liquid is mixed with the whole blood, which is then supplied to the centrifuge bowl E1.

The first open/close valve V1 is then closed to temporarily stop the drawing of whole blood and to circulate the plasma to return to the centrifuge bowl E1, where the circulation speed is gradually increased (S109: acceleration step). The circulation speed is first increased from 60 ml/min to 150 ml/min, and eventually to 200 ml/min.

When the circulation speed exceeds 150 ml/min in the acceleration step, platelets starts to flow out. When the turbidity sensor C2 detects the outflow of platelets, as illustrated in FIG. 28, the eighth open/close valve V8 is opened to store platelet liquid in the platelet intermediate bag Y3 (S110: PC collecting step).

When the turbidity sensor C2 detects that the outflow of platelets has stopped, the step proceeds to the blood returning step (S111), similarly to the first working example.

When the blood returning is finished, and when the finished cycle is the last cycle (S112: YES), the platelet liquid stored in the platelet intermediate bag Y3 is injected into the platelet bag Y5 through the white blood cell removal filter 11. Then the two tubes of the platelet bag are sealed. The platelet bag Y5 storing high-concentration platelet liquid is thus prepared. Now the entire step is finished. If the finished cycle is not the last cycle (S112: NO), the step proceeds to the first blood drawing step (S102).

As described above in detail, similarly to the first working example, the blood component separation device according to the second working example sets the ACD ratio according to the HCT value of a blood donor so as the ACD concentration in the separated platelet liquid to be at a predetermined value (for example, 19%), thereby keeping the ACD concentration in the collected platelet liquid to be kept at a constant level. The ratio of occurrence of the aggregation of platelets can thus be minimized. As a result, a pharmaceutical preparation of platelet liquid that conforms to the targeted specification for pharmaceutical preparation can be obtained.

The amount of the ACD liquid to be supplied determined by the ACD ratio includes the amount of the ACD liquid supplied in the priming step. So that the ACD liquid can surely be applied to the portion that makes contact with blood in the priming step performed before blood drawing, thereby preventing coagulation in blood when introduced.

The embodiments described above are merely exemplary representations and should not be construed to set any limit on the present invention. It goes without saying that various modifications and alterations can be made without departing from the spirit and scope of the present invention. Although the ACD liquid is used as the anticoagulant in the embodiments, other anticoagulants, such as CPD liquid, CPD-A1 liquid, or heparin sodium liquid may be used.

REFERENCE SIGNS LIST 1 blood component separation circuit
9 sterilizing filter
10 bottle needle
15 controller
30 blood component separation circuit
E1 centrifuge bowl
Y1 plasma bag (first container)
Y2 temporary storage bag (second container)
Y3 platelet intermediate bag (third container)
Y4 air bag
Y5 platelet bag
Y6 air bag
C2 turbidity sensor
C4 interface sensor
P1 first blood pump
P2 second blood pump
P3 third blood pump
P4 ACD pump
V1 first open/close valve
V2 second open/close valve
V3 third open/close valve
V4 fourth open/close valve
V5 fifth open/close valve
V6 sixth open/close valve V7 seventh open/close valve
V8 eighth open/close valve
V9 ninth open/close valve
V10 tenth open/close valve
T1 to T21 tube

The invention claimed is:

1. A method for controlling a blood component separation device comprising
selecting a predetermined blood component to be collected in a collected volume, said predetermined blood component comprising platelets;
selecting a concentration of an anticoagulant to be collected with said predetermined blood component in said collected volume;
supplying supplied anticoagulant to whole blood withdrawn from a donor in a selected ratio of an amount of the anticoagulant to an amount of withdrawn whole blood, such that the collected volume of said predetermined blood component contains said selected concentration of anticoagulant; and
separating at least said predetermined blood component and at least some of said anticoagulant from said whole blood and said supplied anticoagulant; and
collecting said predetermined blood component and said at least some of said anticoagulant into said collected volume,
wherein said selected ratio is 1:7.8 when a donor's hematocrit is 34 or 1:7.9 when a donor's hematocrit is 35 or 1:8.0 when a donor's hematocrit is 36 or 1:8.1 when a donor's hematocrit is 37 or 1:8.3 when a donor's hematocrit is 38 or 1:8.4 when a donor's hematocrit is 39 or 1:8.5 when a donor's hematocrit is 40 or 1:8.7 when a donor's hematocrit is 41 or 1:8.8 when a donor's hematocrit is 42 or 1:9.0 when a donor's hematocrit is 43.

2. The method according to claim 1 wherein said step of separating at least said predetermined blood component from said whole blood further comprises
steps (a), (b), (c), and (d), wherein
step (a) is a centrifugal separation step of introducing said whole blood withdrawn from said donor into a centrifugal separator to separate whole blood into a plurality of blood components,
step (b) is a circulation flow step of reintroducing a first blood component, said first blood component comprising at least plasma into the centrifugal separator together with additional whole blood,
step (c) is a circulation/acceleration step, performed after a predetermined amount of the first blood component is separated in the circulation flow step, said circulation/acceleration step comprising stopping supply of whole blood to the centrifugal separator and reintroducing only the first blood component into the centrifugal separator, further performing circulation for a predetermined period of time, and then increasing a circulation speed so that said selected predetermined blood component is separated by the centrifugal separator and collected in said collected volume, and
step (d) is a blood returning step, performed after collecting a predetermined amount of said selected predetermined blood component in the circulation/acceleration step, said blood returning step comprising returning blood components, which are not collected, to said donor, and wherein
steps (a), (b), (c), and (d) are performed as one cycle a plurality of times.

3. The method for controlling according to claim 2, wherein
the circulation/acceleration step includes
a first collecting step of transferring a portion of said selected predetermined blood component with low-concentration of platelets to a temporary storage container, and
a second collecting step of collecting a portion of said selected predetermined blood component with high-concentration of platelets, and wherein
said selected predetermined blood component with low-concentration of platelets transferred to the temporary storage container is reintroduced into the centrifugal separator together with whole blood drawn from said donor in a following cycle.

4. The method according to claim 1, further comprising
a priming step of supplying the anticoagulant, before blood drawing, to a centrifugal separator via a tube coupled to a blood drawing needle, and
said amount of the anticoagulant supplied in said selected ratio of said amount of anticoagulant to said withdrawn whole blood includes an amount of the anticoagulant supplied in the priming step.

5. The method according to claim 4 wherein said step of separating at least said predetermined blood component from said whole blood further comprises steps (a), (b), (c), and (d), wherein
step (a) is a centrifugal separation step of introducing said whole blood withdrawn from said donor into a centrifugal separator to separate whole blood into a plurality of blood components,
step (b) is a circulation flow step of reintroducing a first blood component, said first blood component comprising at least plasma, into the centrifugal separator together with additional whole blood,
step (c) is a circulation/acceleration step, performed after a predetermined amount of the first blood component is separated in the circulation flow step, said circulation/acceleration step comprising stopping supply of whole blood to the centrifugal separator and reintroducing only the first blood component into the centrifugal separator, further performing circulation for a predetermined period of time, and then increasing a circulation speed so that said selected predetermined blood component is separated by the centrifugal separator and collected in said collected volume, and
step (d) is a blood returning step, performed after collecting a predetermined amount of said selected predetermined blood component in the circulation/acceleration step, said blood returning step comprising returning blood components, which are not collected, to said donor, and wherein
steps (a), (b), (c), and (d) are performed as one cycle a plurality of times.

6. The method for controlling a blood component separation device according to claim 5, wherein
the circulation/acceleration step includes
a first collecting step of transferring a portion of said selected predetermined blood component with low-concentration of platelets to a temporary storage container, and
a second collecting step of collecting a portion of said selected predetermined blood component with high-concentration, and wherein
said selected predetermined blood component with low-concentration of platelets transferred to the temporary storage container is reintroduced into the centrifugal separator together with whole blood drawn from said donor in a following cycle.

7. The method for controlling a blood component separation device according to claim 1, wherein the step of selecting a concentration of an anticoagulant comprises selecting a concentration of acid-citrate-dextrose ("ACD"), and the step of selecting a predetermined blood component comprises selecting a platelet liquid.

8. The method according to claim 1 wherein said predetermined blood component comprises platelets and selecting said concentration of anticoagulant comprises selecting a concentration of anticoagulant to reduce a rate of occurrence of aggregation of platelets in said collected volume.

* * * * *